(12) United States Patent
Groh et al.

(10) Patent No.: US 11,478,346 B2
(45) Date of Patent: *Oct. 25, 2022

(54) EMBOLIC PROTECTION CATHETER AND RELATED DEVICES AND METHODS

(71) Applicant: EmStop Inc., Brainerd, MN (US)

(72) Inventors: Mark Groh, Fairview, NC (US); Cinnamon Buckels Larson, Carrboro, NC (US); Yen Liao, Cary, NC (US)

(73) Assignee: EmStop Inc., Brainerd, MN (US)

( * ) Notice: Subject to any disclaimer, the term of this patent is extended or adjusted under 35 U.S.C. 154(b) by 411 days.

This patent is subject to a terminal disclaimer.

(21) Appl. No.: 16/703,633

(22) Filed: Dec. 4, 2019

(65) Prior Publication Data

US 2020/0107923 A1 Apr. 9, 2020

Related U.S. Application Data

(63) Continuation of application No. 16/422,532, filed on May 24, 2019, now Pat. No. 10,561,488, which is a
(Continued)

(30) Foreign Application Priority Data

Dec. 21, 2018 (WO) ................ PCT/US2018/067143

(51) Int. Cl.
*A61F 2/01* (2006.01)
*A61F 2/24* (2006.01)
(Continued)

(52) U.S. Cl.
CPC ............ *A61F 2/013* (2013.01); *A61F 2/0105* (2020.05); *A61F 2/2427* (2013.01); *A61M 29/00* (2013.01);
(Continued)

(58) Field of Classification Search
CPC .......... A61F 2/01; A61F 2/0105; A61F 2/011; A61F 2/013; A61F 2/2427
See application file for complete search history.

(56) References Cited

U.S. PATENT DOCUMENTS

| 4,873,978 A | 10/1989 | Ginsburg |
| 5,549,626 A | 8/1996 | Miller et al. |

(Continued)

FOREIGN PATENT DOCUMENTS

| CN | 1347297 | 5/2002 |
| CN | 203154005 | 8/2013 |

(Continued)

OTHER PUBLICATIONS

"Embolic Protection Devices", Endovascular Today, Buyer's Guide, 2012, 1 page.

(Continued)

*Primary Examiner* — Melanie R Tyson
(74) *Attorney, Agent, or Firm* — Kilpatrick Townsend & Stockton LLP

(57) ABSTRACT

Embolic material capture catheters and related devices and methods constrain a distal end portion of an embolic material capture element in an insertion configuration. A method of deploying an embolic material capture element in a blood vessel includes constraining a distal end portion of the embolic material capture element in an insertion configuration via engagement with a dilator assembly. The embolic material capture element, in the insertion configuration, is advanced through the blood vessel. A deployment cap of the dilator assembly is distally advanced relative to a dilator sheath of the dilator assembly to release the distal end portion of the embolic material capture element from engagement with the dilator assembly to reconfigure the embolic material capture element from the insertion con-
(Continued)

figuration to a fully deployed configuration via self-expansion of the embolic material capture element.

21 Claims, 18 Drawing Sheets

Related U.S. Application Data continuation-in-part of application No. PCT/US2018/067143, filed on Dec. 21, 2018.

(60) Provisional application No. 62/611,454, filed on Dec. 28, 2017.

(51) Int. Cl.
*A61M 29/00* (2006.01)
*A61F 2/82* (2013.01)

(52) U.S. Cl.
CPC ............... *A61F 2/011* (2020.05); *A61F 2/82* (2013.01); *A61F 2002/018* (2013.01); *A61F 2210/0014* (2013.01)

(56) References Cited

U.S. PATENT DOCUMENTS

| | | | |
|---|---|---|---|
| 5,662,671 | A | 9/1997 | Barbut et al. |
| 5,769,816 | A | 6/1998 | Barbut et al. |
| 5,957,949 | A | 9/1999 | Leonhardt et al. |
| 5,993,469 | A | 11/1999 | McKenzie et al. |
| 6,287,321 | B1 | 9/2001 | Jang |
| 6,361,545 | B1 | 3/2002 | Macoviak et al. |
| 6,395,014 | B1 | 5/2002 | Macoviak et al. |
| 7,153,320 | B2 | 12/2006 | Euteneuer et al. |
| 7,344,515 | B2 | 3/2008 | Coyle |
| 7,749,245 | B2 | 7/2010 | Cohn et al. |
| 7,854,746 | B2 | 12/2010 | Dorn et al. |
| 8,323,327 | B2 | 12/2012 | Bei et al. |
| 8,372,108 | B2 | 2/2013 | Lashinski |
| 8,430,902 | B2 | 4/2013 | Bergheim |
| 8,518,073 | B2 | 8/2013 | Lashinski |
| 8,562,639 | B2 | 10/2013 | Khosravi et al. |
| 8,753,370 | B2 | 6/2014 | Lashinski |
| 8,758,388 | B2 | 6/2014 | Pah |
| 8,979,870 | B2 | 3/2015 | Richardson |
| 9,089,406 | B2 | 7/2015 | Basu et al. |
| 9,592,111 | B2 | 3/2017 | Groh |
| 9,622,846 | B2 | 4/2017 | Don Michael |
| 9,675,488 | B2 | 6/2017 | Newell et al. |
| 10,327,898 | B2 | 6/2019 | Groh |
| 10,561,488 | B2 * | 2/2020 | Groh .................. A61F 2/013 |
| 2003/0208224 | A1 | 11/2003 | Broome |
| 2004/0167568 | A1 | 8/2004 | Boyle et al. |
| 2005/0137696 | A1 | 6/2005 | Salahieh et al. |
| 2006/0129180 | A1 | 6/2006 | Tsugita et al. |
| 2007/0043420 | A1 * | 2/2007 | Lostetter .................. A61F 2/95 623/1.11 |
| 2008/0132989 | A1 | 6/2008 | Snow et al. |
| 2009/0163846 | A1 | 6/2009 | Aklog et al. |
| 2010/0241214 | A1 | 9/2010 | Holzer et al. |
| 2013/0041400 | A1 | 2/2013 | Brady et al. |
| 2013/0131787 | A1 | 5/2013 | Ginn |
| 2013/0253571 | A1 | 9/2013 | Bates |
| 2013/0345627 | A1 | 12/2013 | Angel et al. |
| 2014/0018912 | A1 | 1/2014 | Delaloye et al. |
| 2014/0067050 | A1 | 3/2014 | Costello et al. |
| 2014/0088634 | A1 | 3/2014 | Sanati |
| 2014/0277096 | A1 | 9/2014 | Richter et al. |
| 2015/0073526 | A1 | 3/2015 | Kluck |
| 2016/0296730 | A1 | 10/2016 | Zhou et al. |
| 2016/0317276 | A1 | 11/2016 | Groh |

FOREIGN PATENT DOCUMENTS

| | | |
|---|---|---|
| CN | 104039381 | 9/2014 |
| CN | 104540471 | 4/2015 |
| EP | 1154738 | 11/2001 |
| EP | 2399640 | 12/2011 |

OTHER PUBLICATIONS

Desai et al., "Transcatheter Valve Replacement for Aortic Stenosis, Balancing Benefits, Risks, and Expectations", JAMA, vol. 308, No. 6, Aug. 8, 2012, pp. 573-574.

Eggebrecht et al., "Risk of Stroke after Transcatheter Aortic Valve Implantation (Tavi): A Meta-Analysis of 10,037 Published Patients", EuroIntervention, vol. 8, May 15, 2012, pp. 129-138.

Ford, "Keystone Heart's TriGuard Lowers Risk of Stroke for TAVR Patients", Medical Device Daily, American College of Cardiology Scientific Session, vol. 19, No. 53, Mar. 18, 2015, 13 pages.

Groh et al., "Transaortic Approach: Impact on Clinical Outcomes for Patients Receiving Transcatheter Aortic Valve Replacement (TAVR)", 51st STS Meeting, Jan. 24-28, 2015, 12 pages.

Kereiakes et al., "A Novel Filter-Based Distal Embolic Protection Device for Percutaneous Intervention of Saphenous Vein Graft Lesions", JACC: Cardiovascular Interventions, vol. 1, No. 3, Jun. 2008, pp. 248-257.

Mack et al., "Outcomes Following Transcatheter Aortic Valve Replacement in the United States", JAMA, vol. 310, No. 19, Nov. 20, 2013, pp. 2069-2077.

Nietlispach et al., "An Embolic Deflection Device for Aortic Valve Interventions", JACC: Cardiovascular Interventions, vol. 3, No. 11, Nov. 2010, pp. 1133-1138.

Russo et al., "Trans-Aortic Transcatheter Aortic Valve Replacement with Edwards Sapier Ascendra 3", The Cardiothoracic Surgery Network, Apr. 10, 2014, 8 pages.

Werner et al., "First Clinical Experience with the GARDEX EPD: A Novel Embolic Protection Device for Carotid Artery Stenting", EuroIntervention, vol. 8, Jan. 22, 2013, pp. 1026-1032.

Ye, "Cerebral Embolic Protection During TAVI", TAVI Summit, 2013, 26 pages.

* cited by examiner

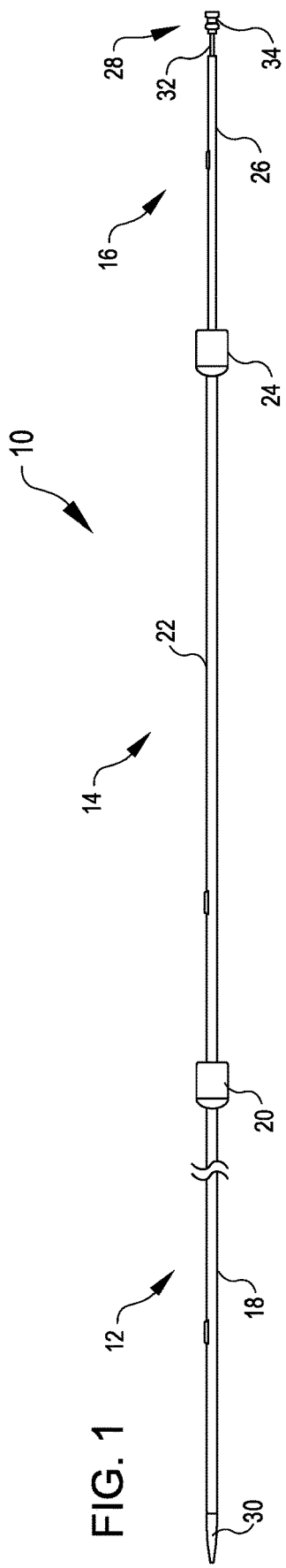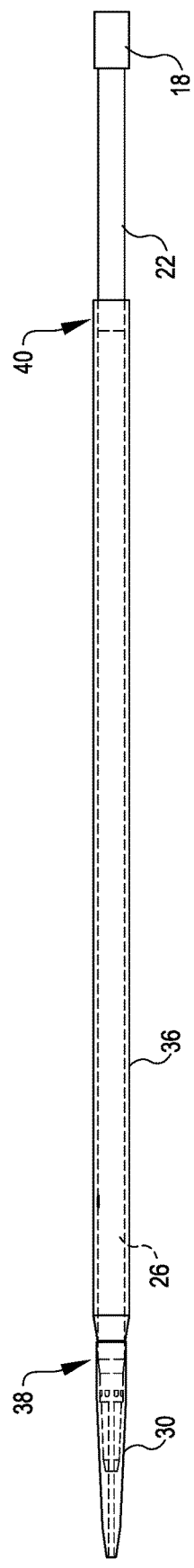

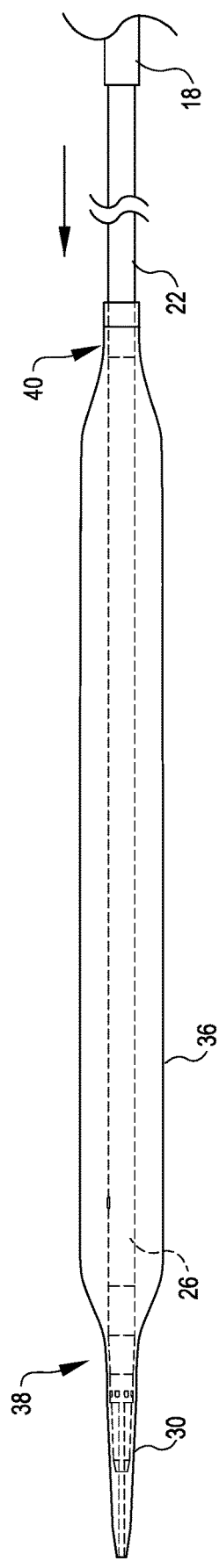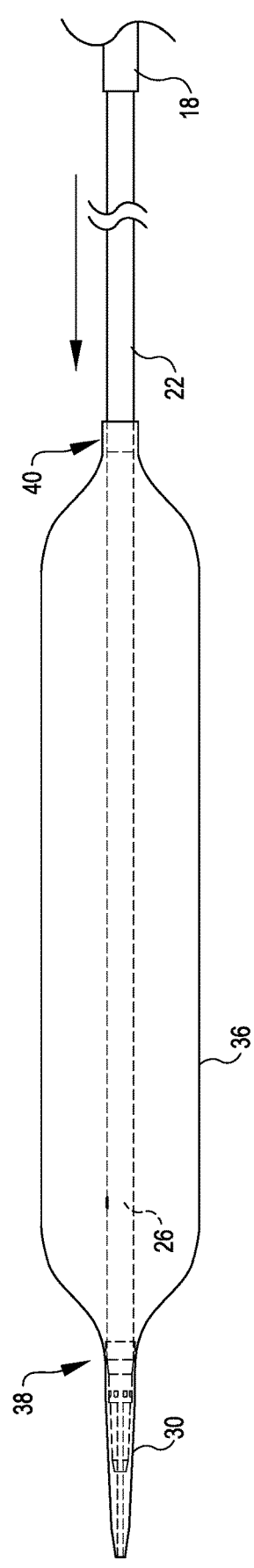

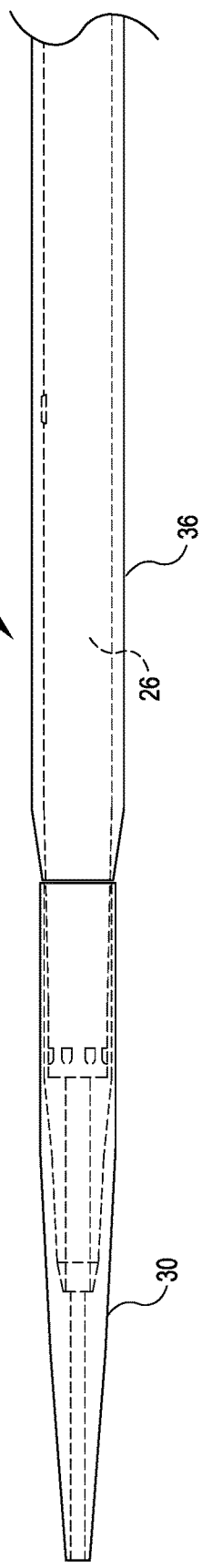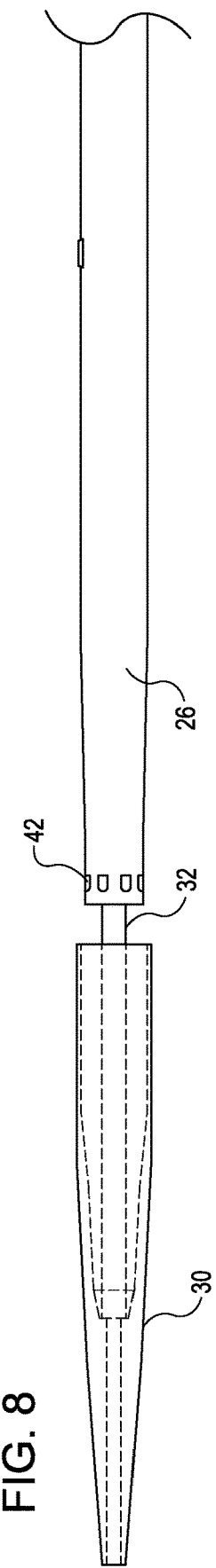
FIG. 7
FIG. 8

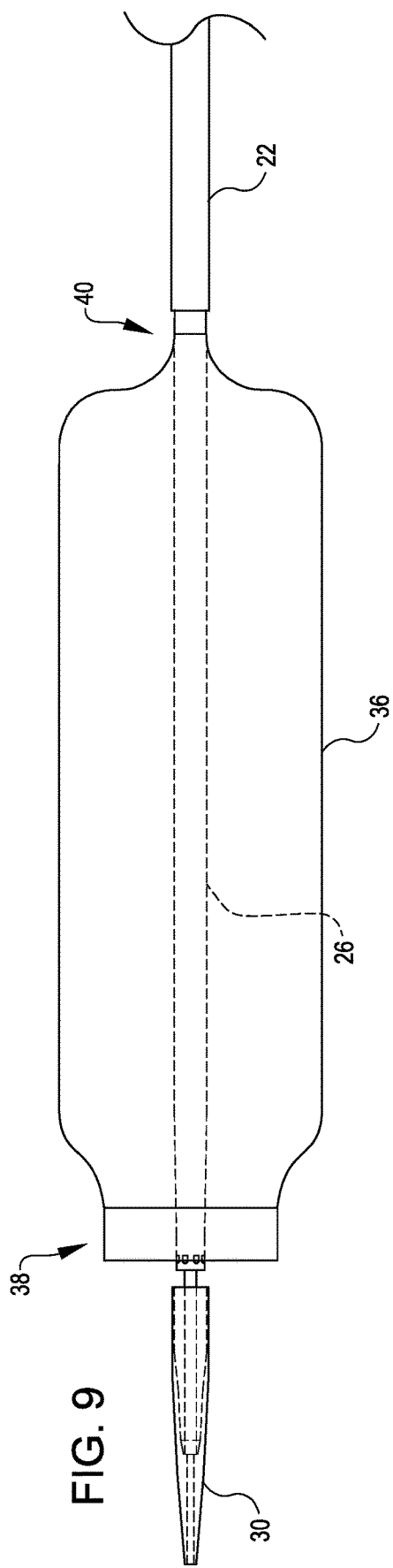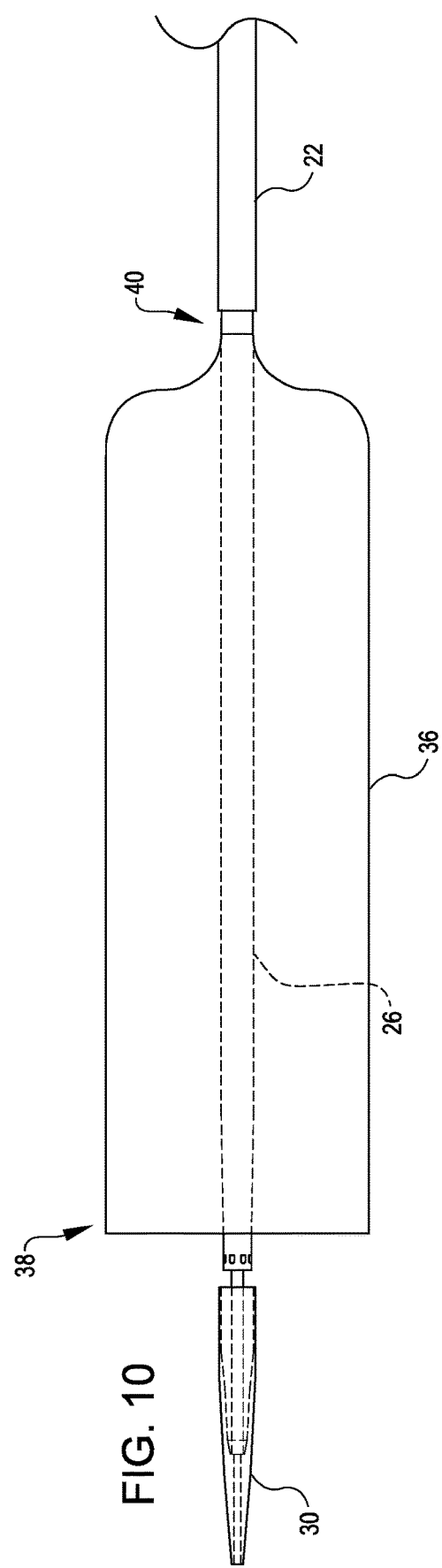

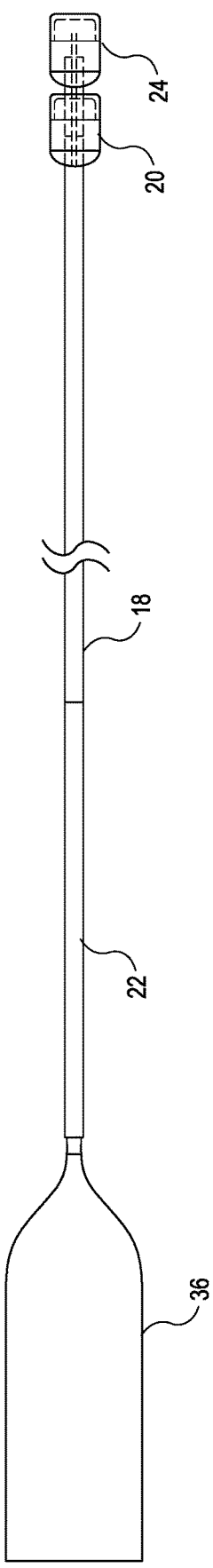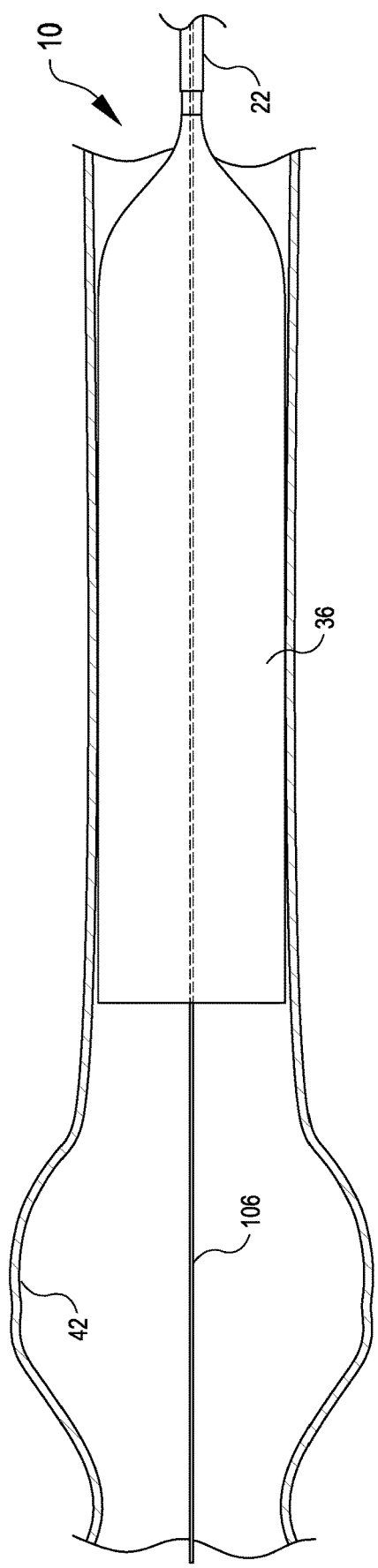
FIG. 11
FIG. 12

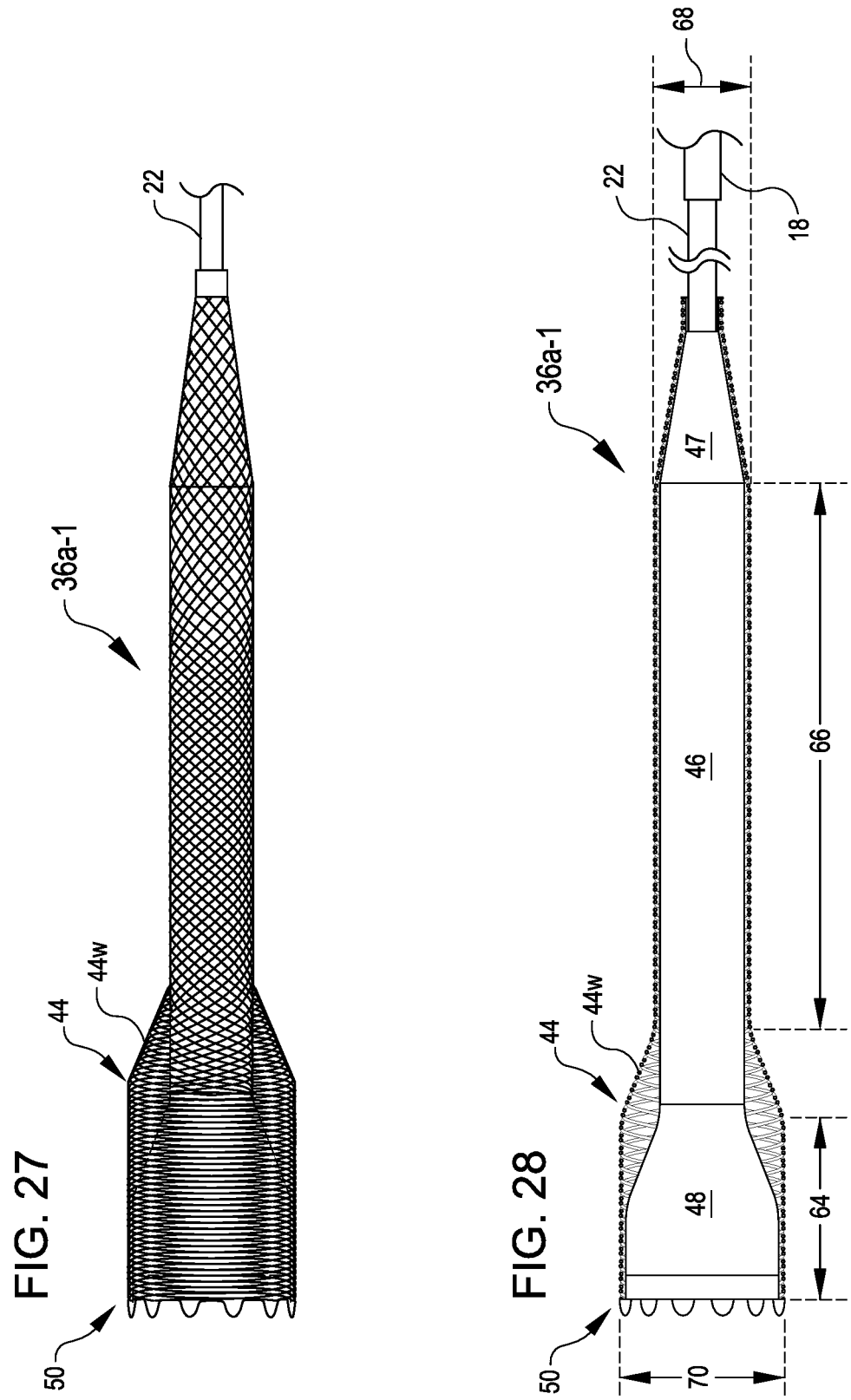

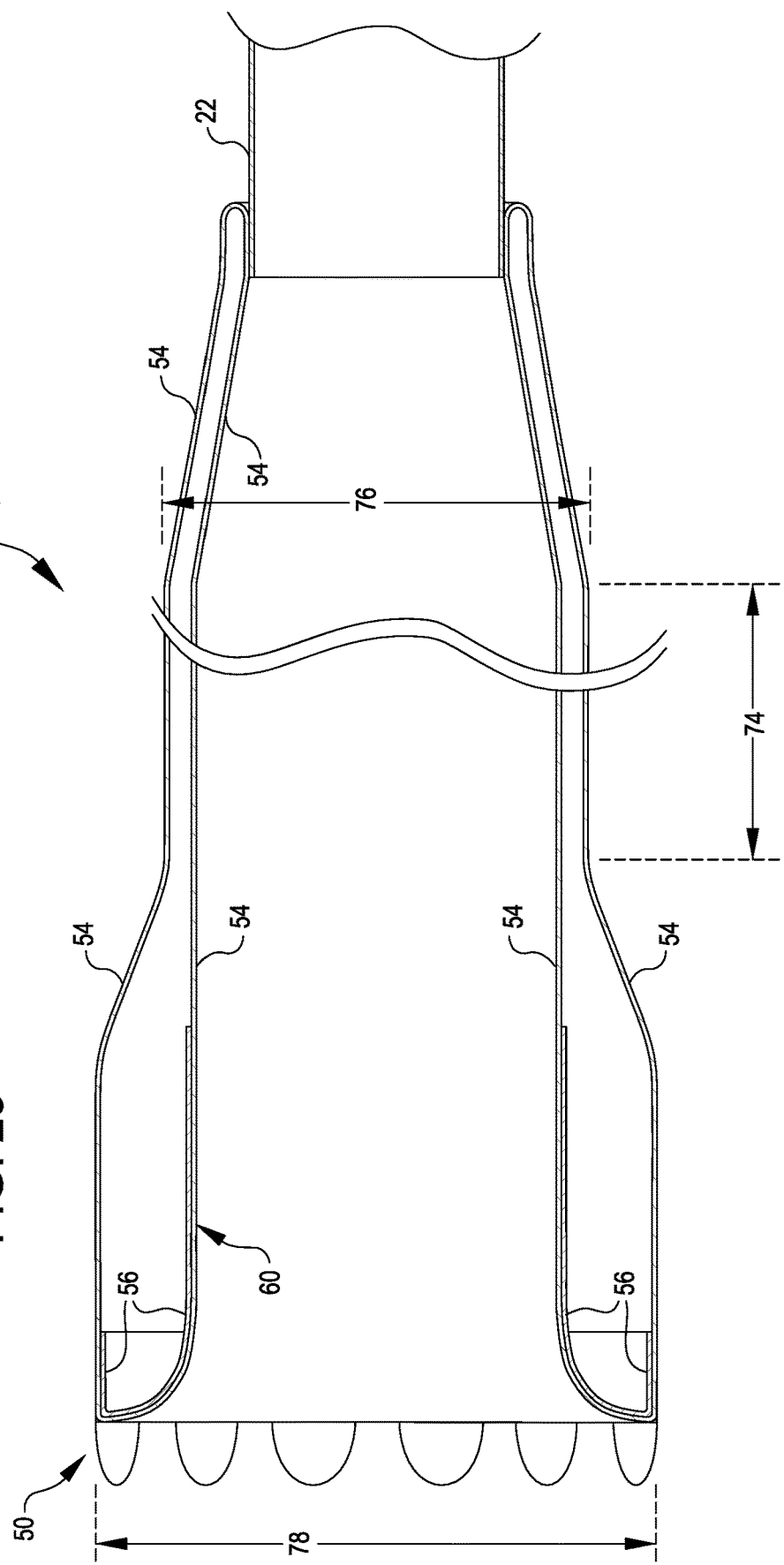

EMBOLIC PROTECTION CATHETER AND RELATED DEVICES AND METHODS

CROSS-REFERENCES TO RELATED APPLICATIONS

This application is a continuation of U.S. patent application Ser. No. 16/422,532, filed May 24, 2019, which application is a Continuation-in-Part of PCT/US2018/067143, filed Dec. 21, 2018, which application claims the benefit of U.S. Provisional Application No. 62/611,454, filed Dec. 28, 2017, the entire contents of which are hereby incorporated by reference in their entirety for all purposes.

BACKGROUND

Transcatheter aortic valve replacement (TAVR) is a proven strategy for the treatment of severe aortic stenosis that has been validated for use in patients who are not eligible for surgical aortic valve replacement (SAVR) due to patient frailty or associated high operative risk. TAVR with the use of a self-expanding or balloon-expanded bioprosthetic valve has been FDA-approved for commercial use in the US in selected patients. TAVR is rapidly becoming the method of choice to treat aortic stenosis in patients deemed to be at increased risk of death if offered a traditional surgical aortic valve replacement. Patients presently selected for TAVR, however, are most often elderly with frailty and a number of comorbidities. The femoral artery is generally the first choice for access to the aortic valve. In patients with significant arterial occlusive disease, however, marked tortuosity of the ileo femoral system and/or significant at risk atheromatous plaque within the native aorta and/or aneurysmal disease may present significant risk for femoral access such that alternate access TAVR is preferable. An alternative route has been proposed several years ago in the form of a trans-apical (TA) approach through the apex of the left ventricle exposed through a left lateral thoracotomy. The TA approach, however, requires opening the left chest in patients having potential pulmonary dysfunction and the rate of bleeding complications may be higher than that observed after traditional trans-femoral (TF) approach. In the search for yet another alternative to compromised peripheral arterial vascular access, a direct trans-aortic (TAo) route has been described in a limited number of cases since 2010. In a recent report, the cases performed through a TAo route represented only 4% of the TAVR cases performed by 2013.

Although results have been encouraging with TAVR, the risk of stroke has been demonstrated to be significantly higher with TAVR relative to SAVR. Clinically observed stroke (CVA) underestimates the prevalence of embolic events inherent with TAVR. During TAVR, stent and implanted valve expansion (with or without the use of a balloon) results in native valve compression and radial leaflet displacement that leads to the liberation of tissue and particulate matter that travels distally in the arterial tree. Some of the debris lodges in terminal branches of cerebral vessels and will be evidenced with new onset stroke. Other debris released at the time of TAVR lodge in vessels of the peripheral circulation, renal circulation, coronary circulation, and mesenteric circulation. These patients may manifest clinical scenario of renal failure, mesenteric ischemia, peripheral ischemia, and/or myocardial infarction. Other patients may not have acute clinical deterioration but may suffer late effects due to impaired functional reserve related to sub-clinical embolic events. The occurrence of embolic events during TAVR is a significant impediment to offering the technique to larger lower risk groups of patients.

A number of different approaches have been developed for embolic protection. Existing embolic protection devices are primarily adapted to deflect embolic material from the brachiocephalic vessels or capture embolic material within the brachiocephalic vessels. There are a number of difficulties with these existing embolic protection devices. First, deployment of the devices requires additional time and can conflict with the performance of the valve implantation procedure. Second, deployment of the devices may lead to additional vessel trauma and liberation of embolic material. Third, the deployment of the devices may be difficult and stability of deployment may make protection less than reliable. Fourth, the devices do not protect the brain from all sources of blood flow and particularly posterior cerebral blood flow is not filtered. Fifth, systemic embolization may still occur that may lead to intestinal, renal, and/or peripheral manifestations of ischemic gut, renal insufficiency and/or peripheral ischemia. Sixth, coronary embolization and myocardial infarction may occur due to proximal embolization.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In many embodiments, an embolic material capture catheter includes an integrated embolic material capture element that is deployable within a blood vessel downstream of a treatment site to capture embolic material released from the treatment site from flowing downstream through the blood vessel, thereby preventing associated embolism(s). In many embodiments, the deployment of the embolic material capture element includes an initial deployment phase in which a distal end portion of the embolic material capture element is held in a collapsed configuration while a proximal end portion is advanced distally toward the distal end portion, thereby expanding a middle portion of the embolic material capture element. In many embodiments, following expansion of the middle portion of the embolic material capture element, the distal end portion of the embolic material capture element is released and self-expands into engagement with the blood vessel. In some embodiments, the embolic material capture element is constrained in the insertion configuration via axial tension applied to the embolic material capture element, thereby enabling the embolic material capture catheter to have a reduced diameter and/or increased flexibility since a retaining sheath is not required to retain the embolic material capture element in the insertion configuration. The embolic material capture catheter can be adapted for use in any suitable procedure. For example, the embolic material capture catheter can be used during implantation of a prosthetic aortic valve in which the integrated embolic material capture element is deployed in a patient's aorta downstream of the patient's aortic valve to capture embolic material released during implantation of the prosthetic aortic valve. In many embodiments, the embolic material capture catheter includes a lumen into which a delivery catheter for the prosthetic valve can be inserted to advance the prosthetic valve to a implantation site upstream of the deployed embolic material capture element. In many embodiments, the lumen is configured to accommodate extraction of embolic material captured by the embolic material capture element. In some embodiments, such as embodiments sized for insertion through the femoral artery, removal of embolic material through the lumen of the embolic material capture catheter may not be possible while the delivery catheter for the prosthetic valve is accommodated in the lumen. In such embodiments, removal of embolic material through the lumen of the embolic material capture catheter can be accomplished following removal of the delivery catheter for the prosthetic valve from the lumen of the embolic material capture catheter. The embolic material capture catheter and related treatment catheters, devices, and methods are especially suited for use in TAVR via any suitable access (including, but not limited to, femoral, direct aortic access, brachiocephalic, subclavian, axillary or carotid arteries) that enables accurate positioning of the prosthetic aortic valve.

Thus, in one aspect, an embolic material capture catheter includes an outer sheath, an inner sheath, an embolic material capture element, and a dilator assembly. The outer sheath defines an outer sheath lumen. The inner sheath is slidably disposed in the outer sheath lumen and defines an inner sheath lumen. The embolic material capture element has a proximal end portion and a distal end portion. The proximal end portion is attached to a distal end portion of the inner sheath. The embolic material capture element has an insertion configuration, an intermediate deployment configuration, and a fully deployed configuration. The embolic material capture element is adapted to, in the fully deployed configuration, interface with an inner surface of a blood vessel. In some embodiments, the embolic material capture element is composed of an outer support element and an inner filter element attached to the outer support element. The outer support element can include one or more members that radially expand into contact with the wall of a vessel along which embolic material is to be blocked from traversing. The inner filter element can include a filtering device or filtering membrane configured to prevent emboli of greater than a particular size from passing through the filtering device or the filtering membrane. The outer support element can be configured to provide a framework and stability for the inner filter element to function. The embolic material capture element is adapted to block flow of embolic material through the blood vessel past the embolic material capture element. The dilator assembly includes a dilator sheath and a deployment cap assembly. The dilator sheath is slidably disposed in the inner sheath lumen and defines a dilator sheath lumen. The deployment cap assembly is slidably disposed in the dilator sheath lumen. A distal end portion of the embolic material capture element is restrained in the insertion configuration and the intermediate deployment configuration by the dilator assembly. A middle portion of the embolic material capture element expands radially from the insertion configuration to the intermediate deployment configuration via distal advancement of the inner sheath towards the distal end portion of the embolic material capture element restrained by the dilator assembly. The distal end portion of the embolic material capture element expands radially from the intermediate deployment configuration to the fully deployed configuration in response to release of the distal end portion of the embolic material capture element by the dilator assembly via distal advancement of the deployment cap assembly relative to the dilator sheath. The dilator assembly is removable from the inner sheath lumen while the embolic material capture element is in the fully deployed configuration via proximal retraction of the dilator assembly relative to the inner sheath.

In many embodiments, the embolic material capture catheter can be reconfigured from the fully deployed configuration to a collapsed captured configuration for withdrawal from the patient. For example, in many embodiments, the embolic material capture element is reconfigurable from the fully deployed configuration to a captured configuration in which the embolic material capture element is disposed in the outer sheath lumen via proximal retraction of the inner sheath relative to the outer sheath.

In many embodiments, the embolic material capture element is retained in the insertion configuration without a surrounding retention sheath, thereby enabling the embolic material capture catheter to have a reduced diameter and/or increased flexibility relative to embolic material capture catheters that include a surrounding retention sheath. In many embodiments, the embolic material capture element conforms to an outer surface of the dilator sheath from the proximal end portion of the embolic material capture element to the distal end portion of the embolic material capture element when the embolic material capture element is in the insertion configuration. In many embodiments, the embolic material capture element has an outer surface that extends between the proximal end portion of the embolic material capture element and the distal end portion of the embolic material capture element. In many embodiments, the outer surface of the embolic material capture element is disposable distal to the outer sheath with the embolic material capture element in the insertion configuration.

In some embodiments, the embolic material capture element is made at least partially from a shape-memory material. In some embodiments, the embolic material capture element is retained in the insertion configuration at least partially via axial tension imparted into the embolic material capture element via the dilator assembly and the inner sheath.

In many embodiments, the embolic material capture catheter is adapted for use with a suitable treatment catheter to perform a surgical task upstream of the embolic material capture element in the fully deployed configuration. For example, in many embodiments, the inner sheath accommodates insertion of a treatment catheter into the inner sheath lumen and advancement of a distal portion of the treatment catheter to a position distal to the distal end portion of the embolic material capture element in the fully deployed configuration. In many embodiments, the distal end portion of the treatment catheter is adapted to accomplish a surgical task.

In many embodiments, the embolic material capture catheter is adapted for use during implantation of a prosthetic aortic valve. For example, in many embodiments, the embolic material capture element is adapted to, in the fully deployed configuration, interface with a patient's aorta and substantially block flow of embolic material through the patient's aorta past the embolic material capture element. In many embodiments, the treatment catheter is adapted to deploy a prosthetic aortic valve.

In many embodiments, the embolic material capture catheter is adapted remove embolic material from blood flowing through the blood vessel. For example, in many embodiments, the embolic material capture element includes a filtering membrane adapted to filter embolic material from blood flowing through the filtering membrane. In some embodiments, the embolic material capture catheter is adapted to be coupled with an embolic material extraction device operable to draw embolic material through the inner sheath lumen while the embolic material capture element is in the fully deployed configuration.

In many embodiments, the embolic material capture element includes an outer scaffold portion, an inner filter portion, and an intermediate portion. The outer scaffold portion has an outer scaffold proximal end portion and an outer scaffold distal end portion. The outer scaffold proximal end portion is attached to the filter sheath distal end portion. The outer scaffold portion is configured to self-expand during reconfiguration of the embolic material capture catheter from the restrained insertion configuration to the deployed configuration for engagement with a blood vessel inner surface. The inner filter portion has an inner filter proximal end portion and an inner filter distal end portion. The inner filter proximal end portion is attached to the filter sheath distal end portion. The inner filter portion is configured to capture embolic material from blood that flows through the inner filter portion. The inner filter distal end portion is coupled with the outer scaffold distal end portion via the intermediate portion. In many embodiments, the inner filter portion is separated from the outer scaffold portion by an intervening annular space in the deployed configuration. In some embodiments, the intermediate portion is configured to capture embolic material from blood flowing through the intermediate portion. In some embodiments, the intermediate portion is nonporous. In many embodiments, the intermediate portion has a conical shape configured to direct blood flow into the inner filter portion.

In some embodiments, the outer scaffold portion, the intermediate portion, and the inner filter portion are portions of an integrally formed braided wire member. In such embodiments, the embolic material capture catheter can include a distal end sheet attached to the intermediate portion that is configured to block flow of embolic material through the intermediate portion. In some embodiments, the distal end sheet is nonporous. In some embodiments, the distal end sheet has a porosity adapted to filter embolic material out of blood flowing through the distal end sheet.

In many embodiments, the outer scaffold distal end portion is configured for atraumatic engagement of the blood vessel inner surface. For example, in many embodiments, the outer scaffold portion includes distally extending loops of wires configured for atraumatic engagement of the blood vessel inner surface.

In many embodiments, the embolic material capture element, in the fully deployed configuration, has a stepped outer diametrical profile configured to enhance deployment from the insertion configuration to the fully deployed configuration by substantially isolating contact with the blood vessel to a distal end portion of the embolic material capture element. For example, in many embodiments, the middle portion of the embolic material capture element has a middle portion external diameter in the fully deployed configuration, the distal end portion of the embolic material capture element has a distal end portion external diameter in the fully deployed configuration and the middle portion external diameter is less than the distal end portion external diameter.

In another aspect, method of deploying an embolic material capture element is provided. The method includes constraining a proximal end portion of an embolic material capture element via attachment to a distal end portion of an inner sheath having an inner sheath lumen. A distal end portion of the embolic material capture element is constrained in an insertion configuration of the embolic material capture element and an intermediate deployment configuration of the embolic material capture element via engagement of the distal end portion with a dilator assembly that extends through the inner sheath lumen. The embolic material capture element, in the insertion configuration, is advanced through the blood vessel. The embolic material capture element is reconfigured from the insertion configuration to the intermediate deployment configuration by expanding a middle portion of the embolic material capture element disposed between the proximal end portion of the embolic material capture element and the distal end portion of the embolic material capture element via distal advancement of the inner sheath toward the distal end portion of the embolic material capture element constrained by the dilator assembly. The embolic material capture element is reconfigured from the intermediate deployment configuration to the fully deployed configuration via reconfiguration of the dilator assembly to release the distal end portion of the embolic material capture element from engagement with the dilator assembly and self-expansion of the distal end portion of the embolic material capture element.

In many embodiments, the method includes capturing the embolic material capture element to enable more streamline extraction of the embolic material capture element from the patient. For example, in many embodiments, the method includes reconfiguring the embolic material capture element from the fully deployed configuration to a captured configuration via proximal retraction of the inner sheath relative to an outer sheath to retract the embolic material capture element within an outer sheath lumen of the outer sheath.

In many embodiments of the method, the embolic material capture element is retained in the insertion configuration without a surrounding retention sheath, thereby enabling the embolic material capture catheter to have a reduced diameter and/or increased flexibility relative to embolic material capture catheters that include a surrounding retention sheath. In many embodiments of the method, the embolic material capture element conforms to an outer surface of the dilator assembly from the proximal end portion of the embolic material capture element to the distal end portion of the embolic material capture element when the embolic material capture element is in the insertion configuration. In many embodiments of the method, the embolic material capture element has an outer surface that extends between the proximal end portion of the embolic material capture element and the distal end portion of the embolic material capture element. In many embodiments of the method, the outer surface of the embolic material capture element is disposable distal to the outer sheath when the embolic material capture element is advanced through the blood vessel in the insertion configuration.

In some embodiments of the method, the embolic material capture element is made at least partially from a shape-memory material. In some embodiments, the method includes retaining the embolic material capture element in the insertion configuration at least partially via axial tension imparted into the embolic material capture element via the dilator assembly and the inner sheath.

In many embodiments of the method, the embolic material capture catheter is used with a suitable treatment catheter to perform a surgical task upstream of the embolic material capture element in the fully deployed configuration. For example, in many embodiments, method includes advancing a distal portion of a treatment catheter through the inner sheath lumen to a position distal to the distal end portion of the embolic material capture element in the fully deployed configuration. In many embodiments, the method includes accomplishing a surgical task distal to the distal end of the embolic material capture element in the fully deployed configuration via the treatment catheter. In many embodiments, the method includes interfacing the embolic material capture element in the fully deployed configuration with a patient's aorta, blocking flow of embolic material through the patient's aorta past the embolic material capture element, and deploying a prosthetic aortic valve from the distal end portion of the treatment catheter.

In many embodiments, the method includes removing embolic material from blood flowing through the blood vessel. For example, in many embodiments, the embolic material capture element includes a filtering membrane and the method includes filtering embolic material from blood flowing through the blood vessel via the filtering membrane. In some embodiments, the method includes extracting embolic material through the inner sheath lumen while the embolic material capture element is in the fully deployed configuration.

In another aspect, an embolic material capture catheter includes a filter sheath and a filter assembly. The embolic material capture catheter has a restrained insertion configuration and a deployed configuration. The filter sheath has an inner lumen and a filter sheath distal end portion. The filter assembly is attached to the filter sheath distal end portion. The filter assembly includes an outer scaffold portion, an inner filter portion, and an intermediate portion.

The outer scaffold portion has an outer scaffold proximal end portion and an outer scaffold distal end portion. The outer scaffold proximal end portion is attached to the filter sheath distal end portion. The outer scaffold portion is configured to self-expand during reconfiguration of the embolic material capture catheter from the restrained insertion configuration to the deployed configuration for engagement with a blood vessel inner surface. The inner filter portion has an inner filter proximal end portion and an inner filter distal end portion. The inner filter proximal end portion is attached to the filter sheath distal end portion. The inner filter portion is configured to capture embolic material from blood that flows through the inner filter portion. The inner filter distal end portion is coupled with the outer scaffold distal end portion via the intermediate portion. In many embodiments, the inner filter portion is separated from the outer scaffold portion by an intervening annular space in the deployed configuration. In some embodiments, the intermediate portion is configured to capture embolic material from blood flowing through the intermediate portion. In some embodiments, the intermediate portion is nonporous. In many embodiments, the intermediate portion has a conical shape configured to direct blood flow into the inner filter portion.

In some embodiments, the outer scaffold portion, the intermediate portion, and the inner filter portion are portions of an integrally formed braided wire member. In such embodiments, the embolic material capture catheter can include a distal end sheet attached to the intermediate portion that is configured to block flow of embolic material through the intermediate portion. In some embodiments, the distal end sheet is nonporous. In some embodiments, the distal end sheet has a porosity adapted to filter embolic material out of blood flowing through the distal end sheet.

In many embodiments, the outer scaffold distal end portion is configured for atraumatic engagement of the blood vessel inner surface. For example, in many embodiments, the outer scaffold portion includes distally extending loops of wires configured for atraumatic engagement of the blood vessel inner surface.

In another aspect, an embolic material capture catheter includes a filter sheath and a filter assembly. The embolic material capture catheter has a restrained insertion configuration and a deployed configuration. The filter sheath has an inner lumen and a filter sheath distal end portion. The filter assembly is attached to the filter sheath distal end portion. The filter assembly includes an outer scaffold portion and an inner filter portion. The outer scaffold portion has an outer scaffold proximal end portion and an outer scaffold distal end portion. The outer scaffold proximal end portion is attached to the filter sheath distal end portion. The outer scaffold portion is configured to self-expand during reconfiguration of the embolic material capture catheter from the restrained insertion configuration to the deployed configuration for engagement with a blood vessel inner surface. The inner filter portion has an inner filter proximal end portion. The inner filter portion is attached to outer scaffold portion. The inner filter portion is configured to capture embolic material from blood that flows through the inner filter portion. In some embodiments, the inner filter portion is attached to the outer scaffold portion along an entire length of the outer scaffold portion.

For a fuller understanding of the nature and advantages of the present invention, reference should be made to the ensuing detailed description and accompanying drawings.

BRIEF DESCRIPTION OF THE DRAWINGS

FIG. 1 shows an embolic material capture catheter in an insertion configuration for insertion into and advancement through a blood vessel of a patient, in accordance with many embodiments.

FIG. 2 shows a distal portion of the embolic material capture catheter of FIG. 1 in the insertion configuration.

FIG. 3 shows an initial state of expansion of a middle portion of an embolic material capture element of the embolic material capture catheter of FIG. 1.

FIG. 4 shows an intermediate state of expansion of the middle portion of the embolic material capture element of the embolic material capture catheter of FIG. 1.

FIG. 7 shows a distal portion of the embolic material capture catheter of FIG. 1 in the insertion configuration.

FIG. 8 shows a distal portion of the embolic material capture catheter of FIG. 1 with the deployment cap in the configuration of FIG. 6.

FIG. 9 shows continued self-expansion of the embolic material capture element of the embolic material capture catheter of FIG. 1 from the configuration of FIG. 6.

FIG. 10 shows the embolic material capture element of the embolic material capture catheter of FIG. 1 fully expanded.

FIG. 11 shows the embolic material capture catheter of FIG. 1 with the embolic material capture element fully deployed, dilator removed, and ready for insertion of a treatment catheter to perform a surgical task upstream of the deployed embolic material capture element.

FIG. 12 shows the embolic material capture catheter of FIG. 1 with the embolic material capture element fully deployed within a patient's aorta, dilator removed, and ready for insertion of a treatment catheter to perform a surgical task upstream of the deployed embolic material capture element.

FIG. 27 shows a side view of an embodiment the embolic material capture element of FIG. 18.

FIG. 28 shows a side cross-sectional view of the embodiment of the embolic material capture element of FIG. 27.

FIG. 29 shows a side cross-sectional view of an embodiment of the embolic material capture element of FIG. 24.

Figure 5:
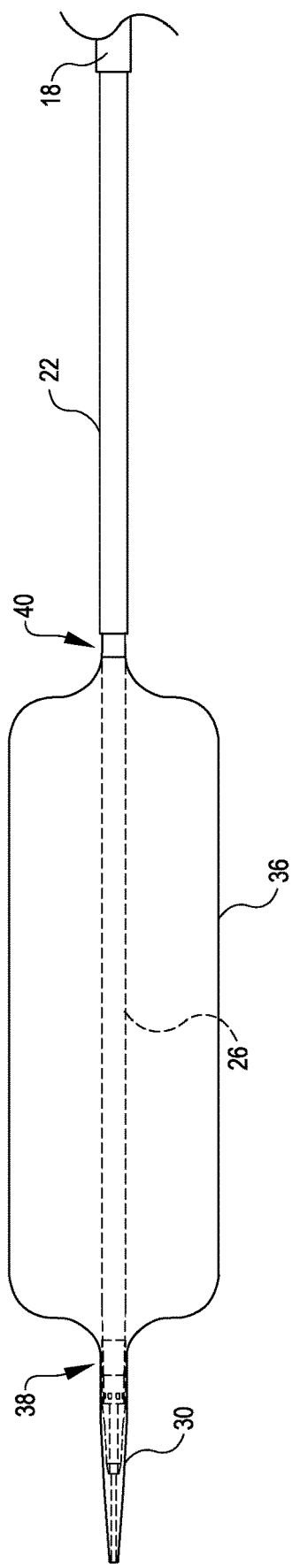
FIG. 5 shows a maximum state of expansion of the middle portion of the embolic material capture element of the embolic material capture catheter of FIG. 1.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Referring now to the drawings, in which like reference numerals represent like parts throughout the several views, FIG. 1 shows an embolic material capture catheter 10 in an insertion configuration for insertion into and advancement through a blood vessel of a patient, in accordance with many embodiments. The catheter 10 includes an outer sheath assembly 12, an inner sheath assembly 14, and a dilator assembly 16. The outer sheath assembly 12 includes an outer sheath 18 and an outer sheath proximal end assembly 20 attached to the outer sheath 18. The outer sheath 18 is a flexible tube having an outer sheath lumen extending through the outer sheath 18. The outer sheath proximal end assembly 20 remains external to the patient and can be used to distally advance the outer sheath 18 through the blood vessel and proximally retract the outer sheath 18 along and/or from the blood vessel. The inner sheath assembly 14 includes an inner sheath 22, an inner sheath proximal end assembly 24 attached to the inner sheath 22, and an embolic material capture element 36 (shown in FIG. 2) attached to the distal end of the inner sheath 22. The inner sheath 22 is a flexible tube having an inner sheath lumen extending through the inner sheath 22. The inner sheath 22 is slidably disposed with the outer sheath lumen of the outer sheath 18. In many embodiments, the outer sheath proximal assembly 20 includes a seal that interfaces with the outer surface of the inner sheath 22 to inhibit and/or prevent escape of bodily fluid (e.g., blood) from an annular space between the inner sheath 22 and the outer sheath 18. The inner sheath proximal end assembly 24 remains external to the patient and can be used to distally advance the inner sheath 22 through the outer sheath 18 and the blood vessel and proximally retract the inner sheath 22 along and/or from the outer sheath 18 and the blood vessel. The dilator assembly 16 includes a dilator sheath 26 and a dilator cap assembly 28. The dilator sheath 26 is a flexible tube having a dilator sheath lumen extending through the dilator sheath 26. The dilator cap assembly 28 includes a dilator cap 30, a dilator shaft 32, and a dilator proximal member 34. The dilator cap 30 is attached to a distal end of the dilator shaft 32. The dilator proximal member 34 is attached to a proximal end of the dilator shaft 32. The dilator shaft 32 extends through and is slidably disposed within the inner sheath lumen of the inner sheath 22. As described herein, a distal end portion of the dilator sheath 26 and the dilator cap 30 engage a distal end portion of the embolic material capture element 36 to restrain the distal end portion of the embolic material capture element 36 when the catheter 10 is in the insertion configuration. By advancing the dilator cap assembly 28 distally relative to the dilator sheath 26, the distal end portion of the embolic material capture element 36 can be released from engagement with the distal end portion of the dilator sheath 26 and the dilator cap 30, thereby allowing self-expansion of the distal end portion of the embolic material capture element 36 as described herein. In many embodiments, the embolic material capture catheter 10 is adapted to be deployed over a guidewire 106 (shown in FIG. 12). For example, the dilator assembly 16 can include a guide wire lumen that extends through the dilator assembly 16.

FIG. 2 shows a distal portion of the embolic material capture catheter 10 in an insertion configuration. The illustrated portion of the catheter 10 includes a distal end portion of the outer sheath 18, a distal end portion of the inner sheath 22 extending distally beyond the lumen of the outer sheath 18, the embolic material capture element 36 in a collapsed insertion configuration, a distal end portion of the dilator sheath 26, and the dilator cap 30. In the illustrated insertion configuration, a distal end portion 38 of the embolic material capture element 36 is trapped between a distal end portion of the dilator sheath 26 and a proximal end portion of the dilator cap 30. With the distal end portion 38 of the embolic material capture element 36 restrained via engagement with the dilator cap 30 and the distal end portion of the dilator sheath 26 and a proximal end portion 40 of the embolic material capture element 36 attached to the distal end of the inner sheath 22, a suitable position of the inner sheath 22 relative to the dilator cap 30 can be maintained to retain the embolic material capture element 36 in the collapsed insertion configuration. For example, in some embodiments, the embolic material capture element 36, in the illustrated collapsed insertion configuration, is under axial tension induced via opposed axial forces applied to the embolic material capture element 36 by the dilator assembly 16 and the inner sheath 22, respectively. In many embodiments, the embolic material capture element 36 conforms to an outer surface of the dilator sheath 26 from the proximal end portion of the embolic material capture element 36 to the distal end portion of the embolic material capture element 36 when the embolic material capture element 36 is in the insertion configuration. In many embodiments, the dilator cap 30 is configured to protect the vasculature during distal advancement of the catheter 10 through the vasculature. In the illustrated configuration, the inner sheath 22 is positioned relative to the outer sheath 18 so that the proximal end of the embolic material capture element 36 is disposed distal to the distal end of the outer sheath 18 and maintained in the collapsed insertion configuration without the use of a sheath surrounding the embolic material capture element 36.

FIG. 3, FIG. 4 and FIG. 5 illustrate progressive expansion of the embolic material capture element 36 from the insertion configuration shown in FIG. 2 to the intermediate deployment configuration shown in FIG. 5 via distal advancement of the inner sheath 22 relative to the dilator assembly 16 while the distal end portion 38 of the embolic material capture element 36 remains restrained by the dilator assembly 16. As shown, a middle portion of the embolic material capture element 36 expands radially from the insertion configuration to the intermediate deployment configuration.

Figure 6:
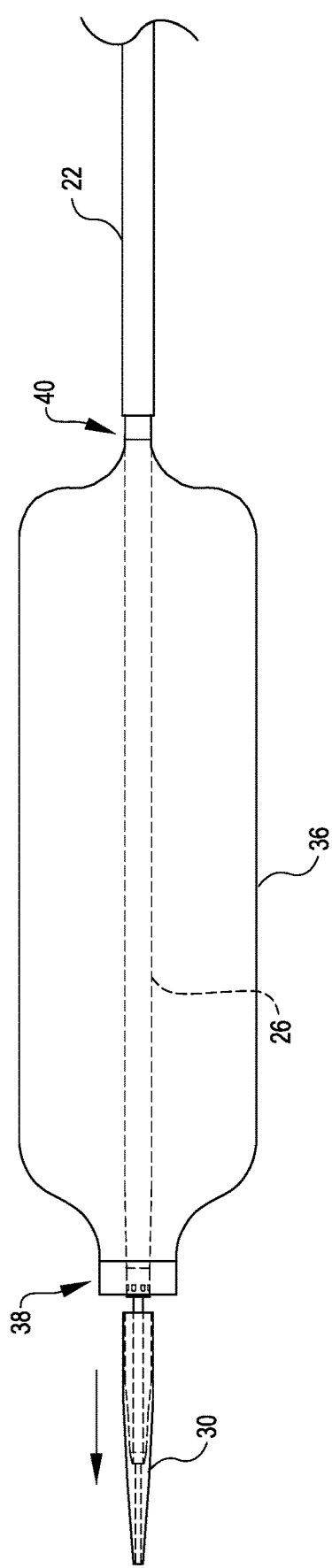
FIG. 6 shows release of the distal end of the embolic material capture element of the embolic material capture catheter of FIG. 1 via distal advancement of a deployment cap relative to the configuration of FIG. 5.

FIG. 6 shows release of the distal end 38 of the embolic material capture element 36 via advancement of the dilator cap assembly 28 relative to the dilator sheath 26, thereby moving the dilator cap 30 distally relative to the distal end of the dilator sheath 26. In many embodiments, upon release of the distal end 38 of the embolic material capture element 36, the distal end 38 self-expands from the intermediate deployment configuration of the embolic material capture element 36 to the configuration shown in FIG. 9 and continues to self-expand to the fully deployed configuration of the embolic material capture element 36 shown in FIG. 10. In many embodiments, the embolic material capture element 36 is made at least partially of a shape-memory material and self-expands from the insertion configuration to the fully deployed configuration in which an outer surface of the embolic material capture element 36 engages an inner surface of the blood vessel.

FIG. 7 and FIG. 8 show close-up views of the distal portion of the embolic material capture catheter 10. FIG. 7 shows the distal portion of the embolic material capture catheter 10 in the insertion configuration. In the insertion configuration, the distal end portion 38 of the embolic material capture element 36 is trapped within a proximal recess in the dilator cap 30 and retained in the proximal recess via the distal end portion of the dilator sheath 26. In the illustrated embodiment, the distal end portion of the dilator sheath 26 includes annularly distributed retention features 42 that protrude radially and are configured to locally engage the distal end portion 38 of the embolic material capture element 36 to enhance retention of the distal end portion 38 within the proximal recess in the dilator cap 30. FIG. 8 shows the distal portion of the embolic material capture catheter 10 with the dilator cap 30 in the release configuration shown in FIG. 6, FIG. 9, and FIG. 10, in which the dilator cap 30 is disposed distal to the distal end portion 38 of the embolic material capture element 36 (not shown).

From the configuration shown in FIG. 10, the dilator assembly 16 can be removed through the inner sheath lumen of the inner sheath 22 to make the inner sheath lumen available for insertion of a treatment catheter through inner sheath lumen of the inner sheath 22 to perform a surgical task upstream of the embolic material capture element 36 in the fully deployed configuration. FIG. 11 shows the embolic material capture catheter 10 with the embolic material capture element 36 in the fully deployed configuration with the dilator assembly 16 removed. Because the inner sheath assembly 16 is advanced distally relative to the outer sheath assembly 12 to deploy the embolic material capture element 36, the inner sheath proximal end assembly 24 can be in close proximity with the outer sheath proximal end assembly 20 when the embolic material capture element 36 is in the fully deployed configuration, thereby enabling the use of existing length treatment catheters.

In some embodiments, the embolic material capture element 36 is composed of an outer support element and an inner filter element attached to the outer support element. The outer support element can include one or more members that radially expand into contact with the wall of a vessel along which embolic material is blocked from traversing. The inner filter element can include a filtering device or filtering membrane configured to prevent emboli of greater than a particular size from passing through the filtering device or the filtering membrane. The outer support element can be configured to provide a framework and stability for the inner filter element to function.

Figure 13:
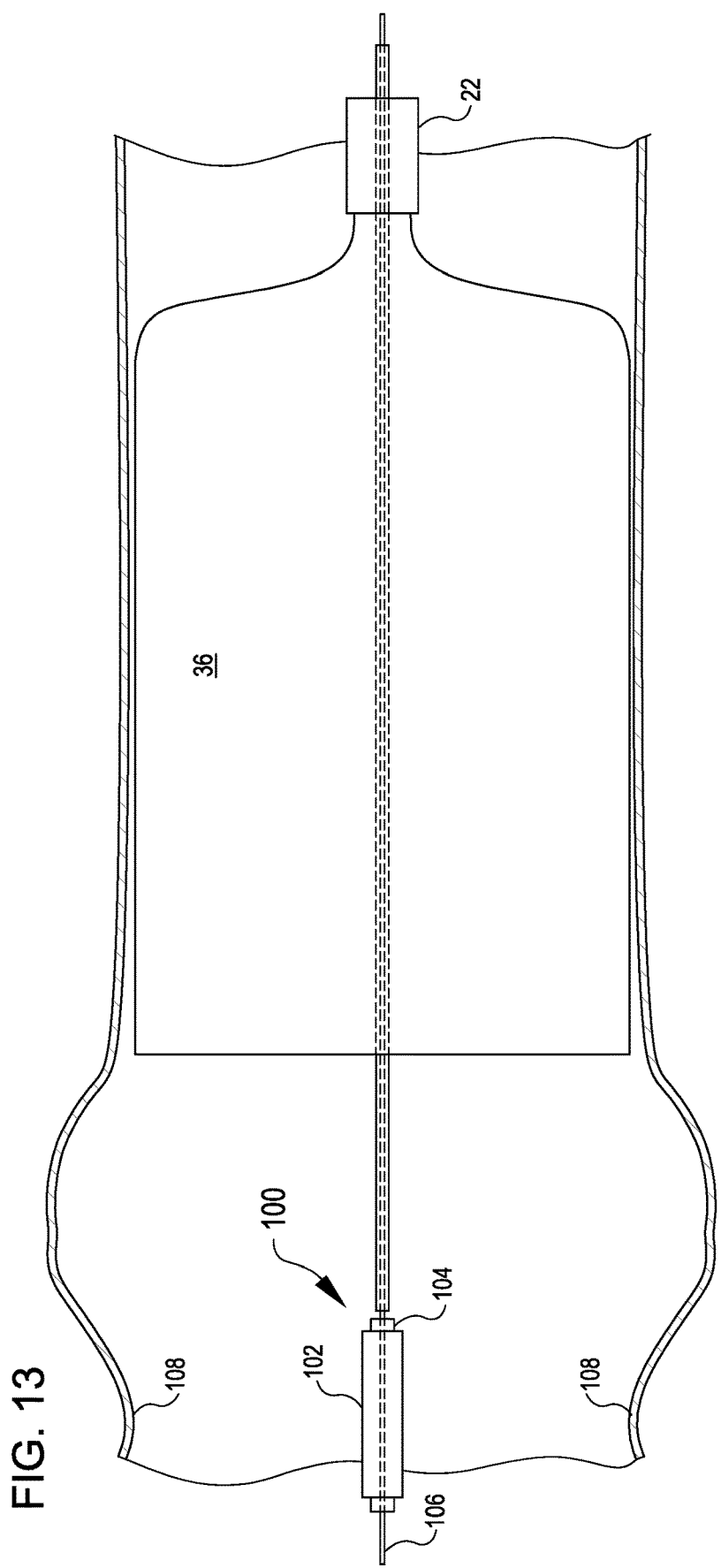
FIG. 13 shows the embolic material capture catheter of FIG. 1 with the embolic material capture element fully deployed within a patient's aorta, dilator removed, and an aortic replacement valve deployment catheter inserted through the embolic material capture catheter and positioned to deploy an aortic replacement valve.

The embolic material capture catheter 10 can be configured for use in any suitable blood vessel and for use with any suitable treatment catheter. For example, FIG. 12 shows an embodiment of the embolic material capture catheter 10 deployed within a patient's aorta 42 to capture embolic material liberated during implantation of a prosthetic aortic valve. FIG. 13 shows the embolic material capture catheter 10 with an aortic replacement valve deployment catheter 100 inserted through the inner sheath lumen of the inner sheath 22 and positioned to deploy an aortic replacement valve 102. The replacement valve deployment catheter 100 includes an expandable member 104 that is expanded to deploy the valve 102. FIG. 13 illustrates the expandable member 104 (and the prosthetic valve 102 mounted to the expandable member 104 in a collapsed configuration) positioned for implantation of the prosthetic valve 102 after being advance along a guide wire 106 and through the inner sheath lumen of the inner sheath 22. With the embolic material capture element 36 deployed downstream of the patient's native aortic valve 108, the embolic material capture element 36 is positioned to capture embolic material released during deployment of the prosthetic aortic valve 102.

Figure 14:
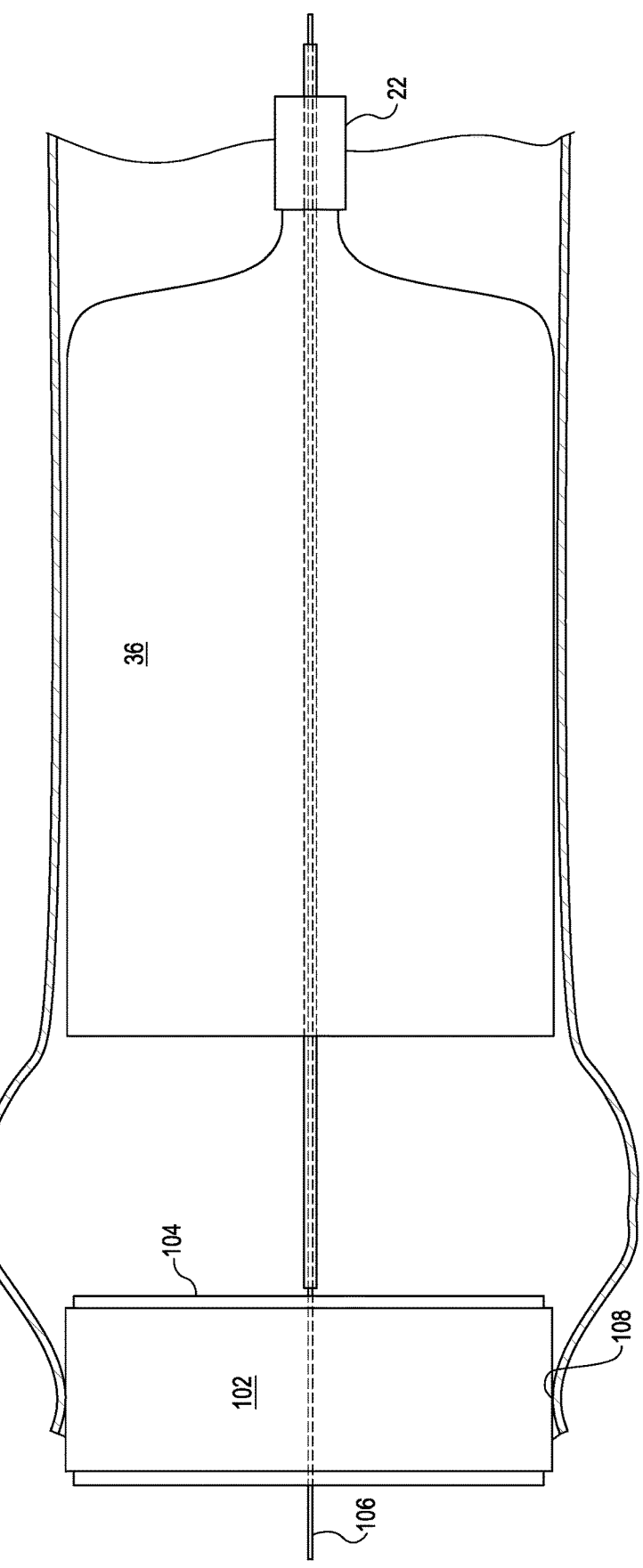
FIG. 14 shows deployment of the aortic replacement valve from the delivery configuration of FIG. 13 via expansion of an expandable member of the aortic replacement valve deployment catheter.

FIG. 14 illustrates deployment of the prosthetic valve 102 at the implantation site via expansion of the expandable member 104. The expansion of the expandable member 104 expands the prosthetic aortic valve 102 into its deployed configuration covering the native aortic valve 108. The expandable member 104 can be expanded during rapid pacing of the patient's heart. Embolic material released during deployment of the prosthetic aortic valve 102 is captured by the embolic material capture element 36. In some embodiments, the embolic material capture catheter 10 can be fluidly coupled with an external embolic material removal device operable to remove embolic material gathered by the embolic material capture element 36 from the patient. Following implantation of the prosthetic aortic valve 102, the replacement valve deployment catheter 100 can be removed from the embolic material protection catheter 10 via proximal retraction through the inner sheath lumen of the inner sheath 22

Figure 15:
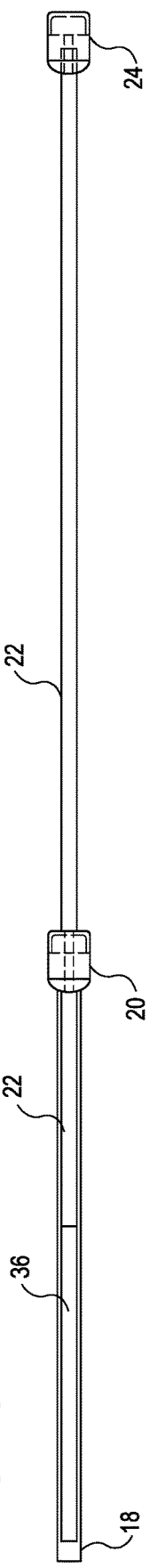
FIG. 15 shows the embolic material capture catheter of FIG. 1 with the embolic material capture element in a captured configuration.

In many embodiments, the embolic material capture catheter 10 can be reconfigured to capture the embolic material capture element 36 prior to withdrawal of the embolic material capture catheter 10 from the patient. For example, in the illustrated embodiment, the embolic material capture catheter 10 can be reconfigured from the configuration shown in FIG. 11 in which the embolic material capture element 36 is in the fully deployed configuration to the configuration shown in FIG. 15 in which the embolic material capture element is in the captured configuration via proximal retraction of the inner sheath assembly 14 relative to the outer sheath assembly 12, thereby pulling the embolic material capture element 36 into the outer sheath lumen of the outer sheath 18.

Figure 16:
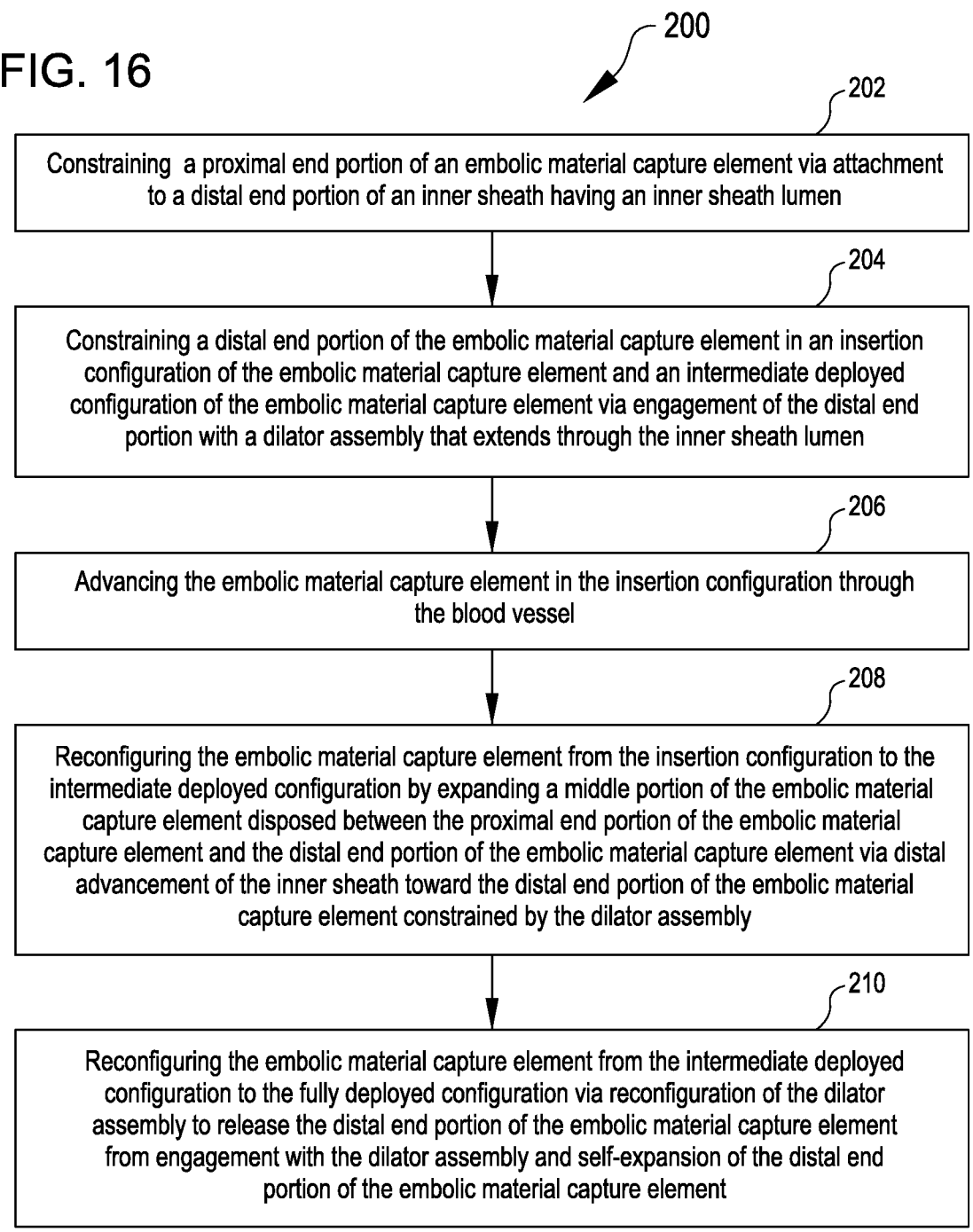
FIG. 16 is a simplified block diagram of acts of a method of deploying an embolic material capture element in a blood vessel, in accordance with many embodiments.

FIG. 16 is a simplified block diagram of acts of a method 200 of deploying an embolic material capture element in a blood vessel, in accordance with many embodiments. The method 200 can be practiced using any suitable device or devices, including the embolic material capture catheter 10 described herein. The method 200 can be used to provide embolic protection in conjunction with any suitable treatment, including the treatments indicated herein.

The method 200 includes constraining a proximal end portion of an embolic material capture element via attachment to a distal end portion of an inner sheath having an inner sheath lumen (act 202). For example, as illustrated in FIG. 2, the proximal end 40 of the embolic material capture element 36 is attached to the distal end of the inner sheath 22 in the embolic material capture catheter 10.

The method 200 further includes constraining a distal end portion of the embolic material capture element in an insertion configuration of the embolic material capture element and an intermediate deployment configuration of the embolic material capture element via engagement of the distal end portion with a dilator assembly that extends through the inner sheath lumen (act 204). For example, in the insertion configuration illustrated in FIG. 2 and the intermediate deployment configuration illustrated in FIG. 5, the distal end portion 38 of the embolic material capture element 38 is constrained via engagement of the distal end portion 38 with the dilator assembly 16, which extends through the inner sheath lumen of the inner sheath 22.

The method 200 further includes advancing the embolic material capture element in the insertion configuration through the blood vessel (act 206). For example, act 206 can be accomplished via advancing the embolic material capture catheter 10 through a blood vessel in either of the insertion configurations shown in FIG. 1 and FIG. 2.

The method 200 further includes reconfiguring the embolic material capture element from the insertion configuration to the intermediate deployment configuration by expanding a middle portion of the embolic material capture element disposed between the proximal end portion of the embolic material capture element and the distal end portion of the embolic material capture element via distal advancement of the inner sheath toward the distal end portion of the embolic material capture element constrained by the dilator assembly (act 208). For example, act 208 can be accomplished via reconfiguring the embolic material capture catheter 10 from the insertion configuration illustrated in FIG. 2 to the intermediate deployment configuration illustrated in FIG. 5 as described herein.

The method 200 further includes reconfiguring the embolic material capture element from the intermediate deployment configuration to the fully deployed configuration via reconfiguration of the dilator assembly to release the distal end portion of the embolic material capture element from engagement with the dilator assembly and self-expansion of the distal end portion of the embolic material capture element (act 210). For example, act 210 can be accomplished via reconfiguring the embolic material capture catheter 10 from the intermediate deployment configuration illustrated in FIG. 5 to the fully deployed configuration illustrated in FIG. 10 as described herein.

Figure 17:
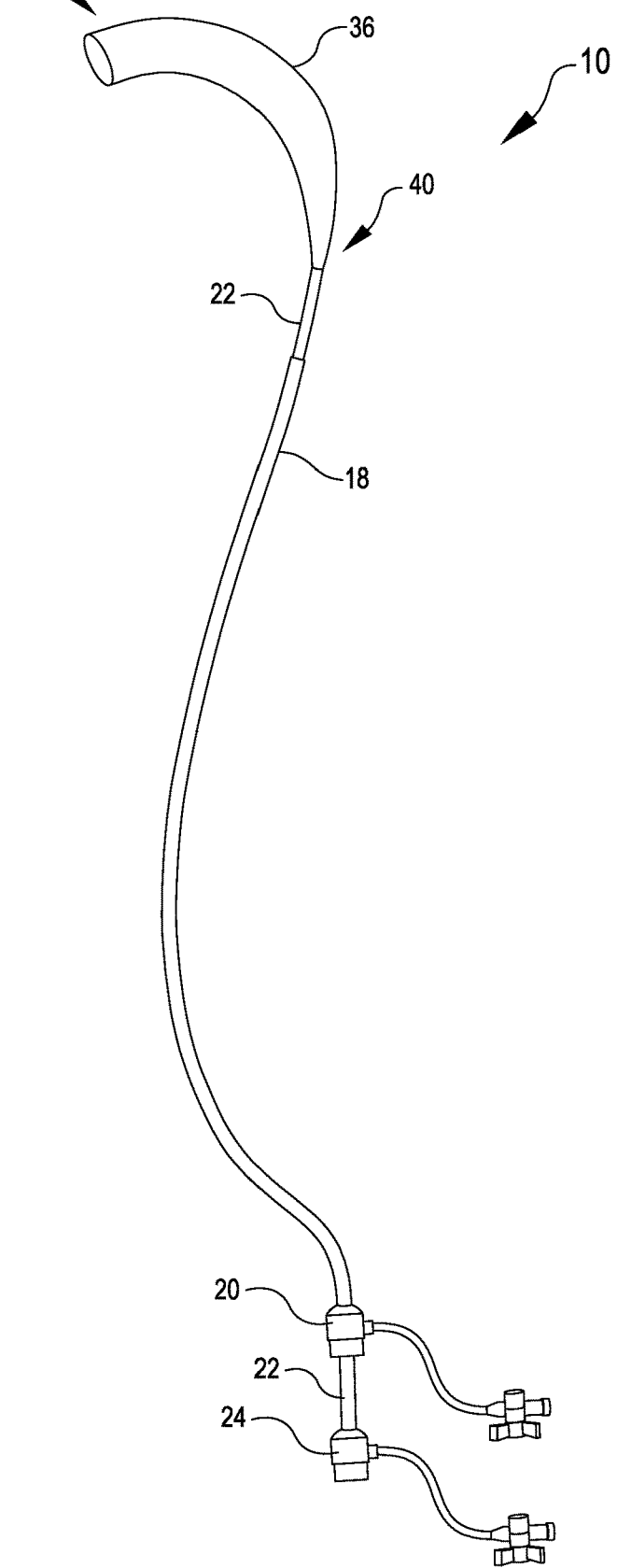
FIG. 17 shows a shape of the embolic material capture catheter of FIG. 1 while deployed within a vasculature of a patient.

FIG. 17 shows a shape of the embolic material capture catheter 10 while deployed within a vasculature of a patient. In many embodiments, the embolic material capture element 36 has a flexibility so as to have a deployed shape in which the distal end portion 38 conforms to the inner surface of the blood vessel (e.g., the aorta 42) and conform to the shape of the blood vessel. For example, in many embodiments, the embolic material capture element 36 is configured to conform to the shape (e.g., curvature) of the blood vessel between the distal end portion 38 and the proximal end portion 40 (e.g., to the curvature of the aorta 42 as illustrated in FIG. 17).

Embolic Material Capture Element Configurations

Figure 18:
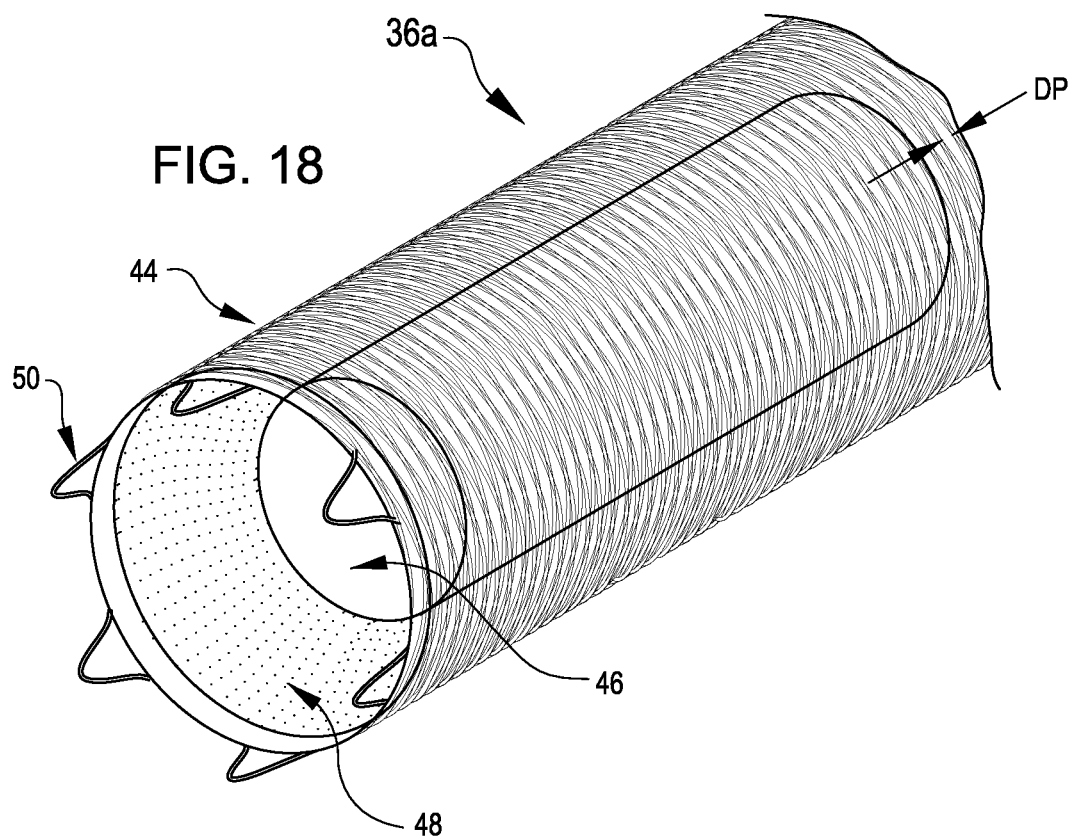
FIG. 18 shows a first configuration of the embolic material capture element of the embolic material capture catheter of FIG. 1.
Figure 19:
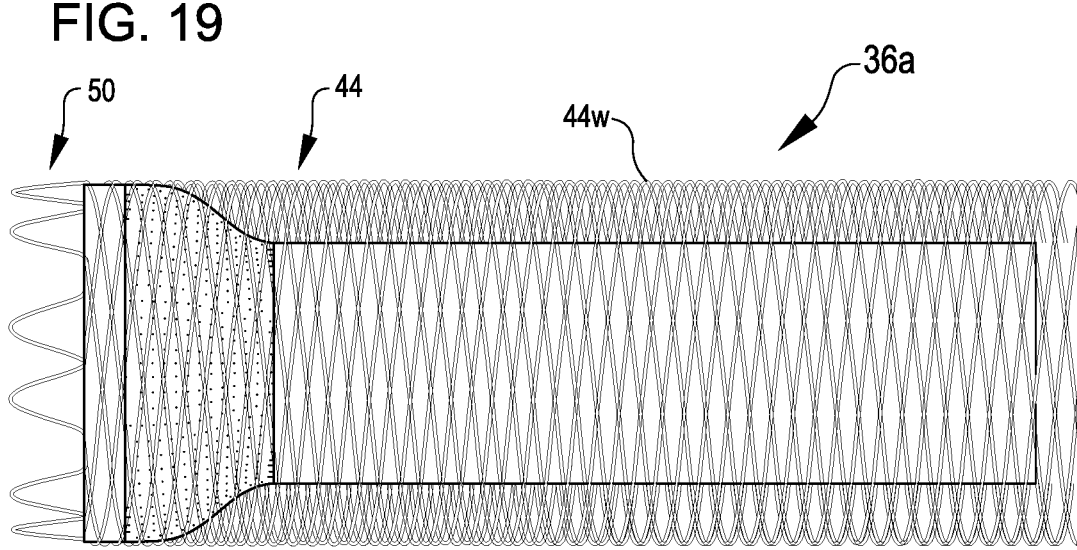
FIG. 19 shows a side view of the embolic material capture element of FIG. 18.
Figure 20:
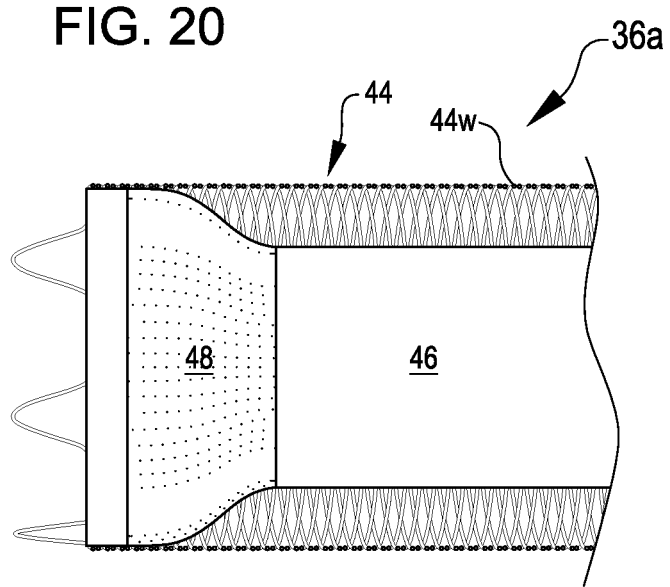
FIG. 20 shows a side cross-sectional view of the embolic material capture element of FIG. 18.

The embolic material capture element 36 can have any suitable configuration. For example, FIG. 18 shows a first configuration 36a of the embolic material capture element 36. The first configuration 36a of the embolic material capture element 36 includes an outer scaffold 44, an inner filter 46, an a connection cone 48 that connects a distal end of the inner filter 46 to the distal end of the outer scaffold 44. FIG. 19 shows a side view of the first configuration 36a the embolic material capture element 36. FIG. 20 shows a side cross-sectional view of the first configuration 36a of the embolic material capture element 36.

The outer scaffold 44 includes one or more inter-braided helically-shaped lengths of a suitable wire 44w (e.g., 0.006 to 0.010 inch diameter wire made from a suitable nickel-titanium shape-memory alloy). In many embodiments, strands of the wire 44w are alternately woven (e.g., passed over and then under) crossing portions of the strands of the wire 44w. From the insertion configuration shown in FIG. 2 to the fully deployed configuration shown in FIG. 18, a pitch between adjacent locations on the wire 44w decreases from a suitable initial pitch to a suitable deployed pitch (DP) and the diameter of the outer scaffold 44 increases from a suitable insertion configuration diameter to a suitable fully deployed configuration diameter, thereby producing a corresponding decrease in the length of the outer scaffold 44. The wire 44w of the outer scaffold 44 has a shape memory such that the outer scaffold 44 automatically reconfigures from the insertion configuration to the fully deployed configuration in response to the distal advancement of the inner sheath 22 and the release of the distal end portion 38 of the first configuration 36a of the embolic material capture element 36. Upon retraction of the first configuration 36a of the embolic material capture element 36 into the outer sheath 18, the pitch between adjacent locations on the wire 44w increases and the diameter of the outer scaffold 44 decreases, thereby producing a corresponding increase in the length of the outer scaffold 44. In the illustrated embodiment, the outer scaffold 44 has an atraumatic leading edge 50 formed by loops of the wire 44w. In some embodiments, the outer scaffold 44 includes capture loops that are engaged with the distal end portion of the dilator sheath 26 and the proximal end portion of the dilator cap 30 while the embolic material capture element 36 is in the insertion configuration. In some embodiments, the maximum expanded diameter of the embolic material capture element 36 is sized to ensure engagement with a patient's aortic arch.

In many embodiments, the inner filter 46 has a suitable porosity that provides for capture of embolic material by the inner filter 46 while accommodating blood flow through the inner filter 46. The inner filter 46 can be made from any suitable material. For example, in some embodiments, the inner filter 46 includes a helically-braided polyethylene terephthalate (PET) filter. In some embodiments, the inner filter 46 includes a helically-braided polymer filter made from a suitable polymer yarn such as ultra-high-molecular-weight polyethylene (UHMWPE), PET, nylon, polypropylene, polytetrafluoroethylene (PTFE), and liquid crystal polymer (LCP). In some embodiments, the inner filter 46 includes a laser cut polymer filter made from a suitable polymer material (e.g., elastomeric materials such as silicones, polyurethanes and co-polymers). In some embodiments, the inner filter 46 includes a woven textile filter with a diameter less than or equal to the braided outer scaffold 44 with target porosity to capture embolic material and allow for blood flow through the inner filter 46. Such a woven textile filter can be made from a suitable polymer yarn such as UHMWPE, PET, nylon, polypropylene, PTFE, and LCP. The inner filter 46 can have any suitable configuration. For example, in many embodiments, the inner filter 46 can have an outer diameter in the fully deployed configuration less than or equal to the inner diameter of the outer scaffold 44 in the fully deployed configuration. In many embodiments, the inner filter 46 has a longitudinal length and/or longitudinal flexibility that accommodates the change in length of the outer scaffold 44 between the insertion configuration and the fully deployed configuration.

The connection cone 48 connects the distal end of the inner filter 46 to the distal end of the outer scaffold 44. In the illustrated embodiment, the diameter of the distal end of the connection cone 48 is larger than the diameter of the proximal end of the connection cone 48. In many embodiments, the connection cone 48 has a shape (e.g., conical) that provides for a smooth transition for blood flow into the distal opening of the inner filter 46. The connection cone 48 can be made from any suitable material. For example, the connection cone 48 can be formed from a suitable polymer sheet. The connection cone 48 can be attached to the outer scaffold 44 and the inner filter 46 using any suitable approach. For example, a distal end portion of the connection cone 48 can be laminated to a corresponding distal end portion of the outer scaffold 44; a proximal end portion of the connection cone 48 can be laminated to a corresponding distal end portion of the inner filter 46. The connection cone 48 can be nonporous or have a suitable porosity that provides for capture of embolic material by the connection cone 48 while accommodating blood flow through the connection cone 48. For example, a suitable porous connection cone 48 can be formed from a laser cut polymer sheet.

The inner filter 46 can be fabricated using any suitable approach. For example, the inner filter 46 can be manufactured as a stand-alone single braid. As another example, the inner filter 46 can be cut from a longer section of tubing that is braided to meet the target porosity of the inner filter 46. In many embodiments, the maximum diameter of the inner filter 46 is less than the deployed diameter of the outer scaffold 44 and the minimum diameter of the inner filter 46 is larger than the delivery catheter for the prosthetic valve.

Figure 21:
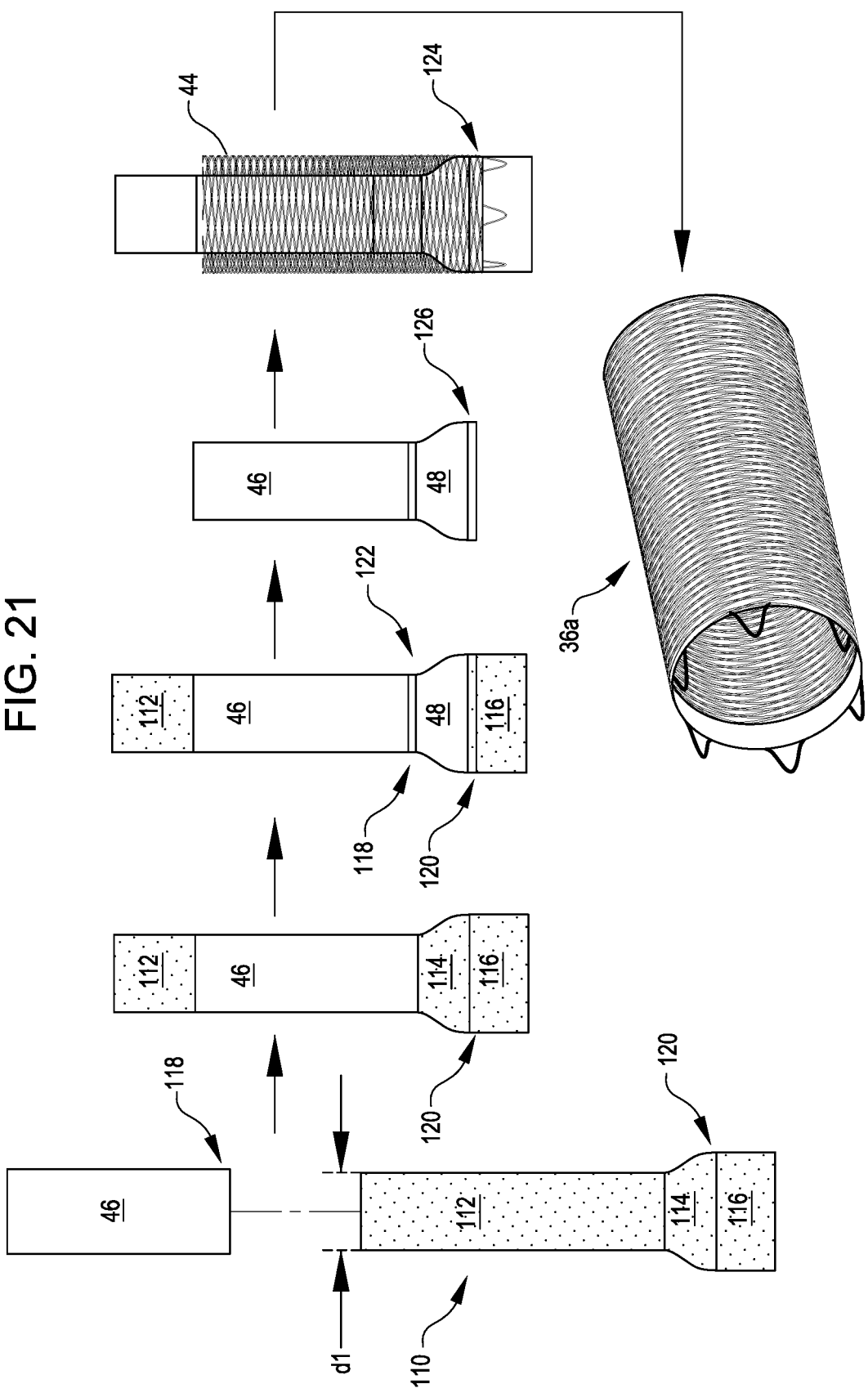
FIG. 21 illustrates a process for fabricating the embolic material capture element of FIG. 18.

The first configuration 36a of the embolic material capture element 36 can be assembled using any suitable approach. For example, referring to FIG. 21, a mandrel 110 having a first cylindrical section 112, a conical section 114, and a second cylindrical section 116 can be employed to assemble the first configuration 36a of the embolic material capture element 36. The mandrel 110 can be made from any suitable material (e.g., a suitable metal or plastic). The first cylindrical section 112 has a diameter (d1) that is selected so that the first cylindrical section 112 can be inserted through the inner filter 46 as illustrated to restrain the inner filter 46 during attachment of the inner filter 46 to the connection cone 48. With the inner filter 46 in the illustrated position on the first cylindrical section 112, the connection cone 48 can be formed onto, or attached to, the inner filter 46 using any suitable approach. For example, in some embodiments, the connection cone 48 is formed on the mandrel 110 (e.g., onto the conical section 114, a distal end portion 118 of the inner filter 46, and a proximal end portion 120 of the second cylindrical section 116) by applying a suitable material (e.g., a suitable polymer material) via dipping or spraying. In many embodiments, the connection cone 48 includes a proximal cylindrical portion 122 that overlaps the distal end portion 118 of the inner filter 46.

The connection cone 48 can alternatively be separately formed. For example, a section of polymer tubing can be attached to the distal end portion 118 of the inner filter 46 via dipping, spraying, or heat setting. The resulting assembly can be placed into a mold and the section of the polymer tubing molded into the shape of the connection cone 48 using any suitable approach (e.g., similar to how some medical catheter balloons are blow molded). The distal end portion of the resulting connection cone 48 can be trimmed to a desired shape after it is removed from the mold. In many embodiments, the proximal cylindrical portion 122 of the connection cone 48 overlaps the distal end portion 118 of the inner filter 46. In embodiments where the connection cone 48 is porous, the connection cone 48 can be laser cut after being formed to add porosity.

With the inner filter 46 attached to the connection cone 48, a distal end portion 124 of the outer scaffold 44 can be attached to a distal end portion 126 of the connection cone 48. The connection cone 48 can be placed inside of the outer scaffold 44 and the distal edges of the connection cone 48 and outer scaffold 44 can be aligned. If the outer scaffold 44 includes capture loops that are engaged with the distal end portion of the dilator sheath 26 and the proximal end portion of the dilator cap 30 while the embolic material capture element 36 is in the insertion configuration, the capture loops can be masked off. The distal end portion 126 of the connection cone 48 can be attached to the distal end portion 124 of the outer scaffold 44 over a desired connection length using any suitable approach, for example, via heating to bond the distal end portions, via dipping in a suitable bonding agent to bond the distal end portions, or spraying of a suitable bonding agent to bond the distal end portions 124, 126. The completed first configuration 36a of the embolic material capture element 36 can then be removed from the mandrel 110.

Figure 22:
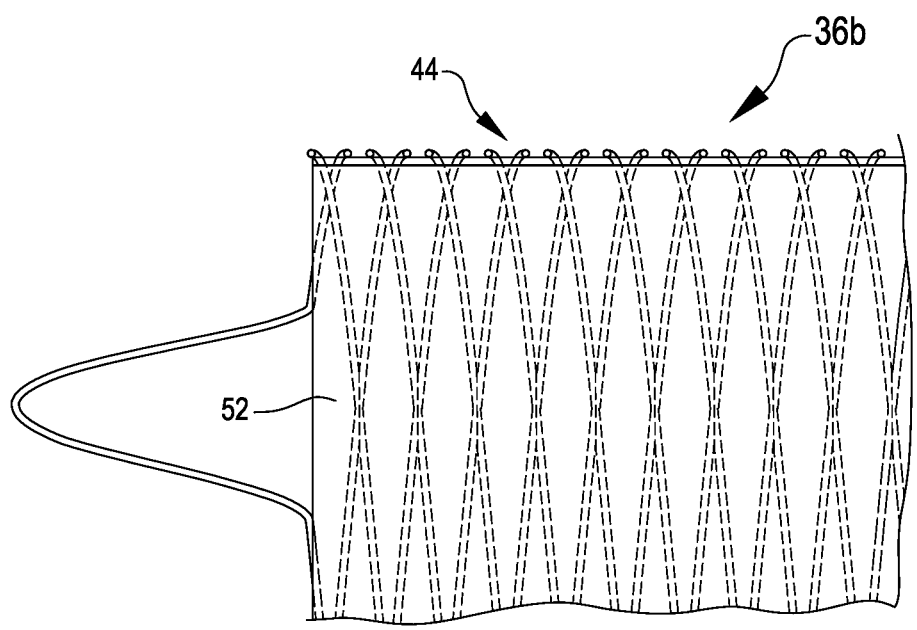
FIG. 22 shows a close-up side view of a second configuration of the embolic material capture element of the embolic material capture catheter of FIG. 1.
Figure 23:
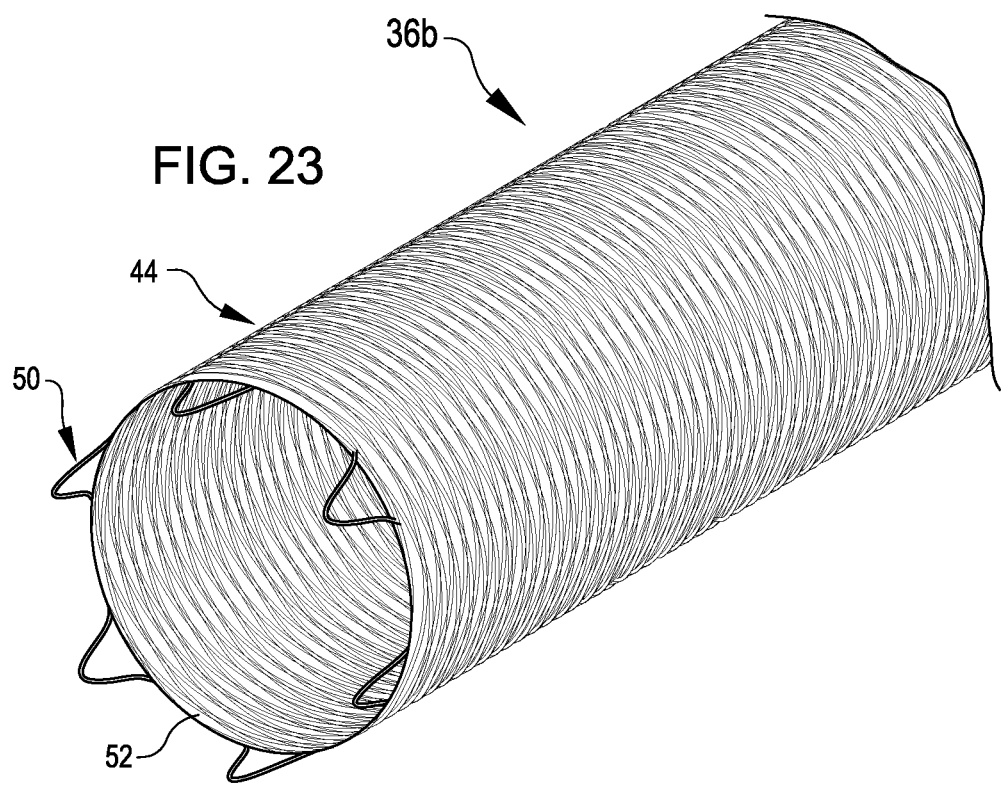
FIG. 23 shows an isometric view of the embolic material capture element of FIG. 22.

FIG. 22 shows a close-up side view of a second configuration 36b of the embolic material capture element 36. The second configuration 36b of the embolic material capture element 36 includes the outer scaffold 44 (which is described above) and an inner filter 52 attached to and supported by the outer scaffold 44. FIG. 23 shows an isometric view of the second configuration 36b of the embolic material capture element 36.

In many embodiments, the inner filter 52 has a suitable porosity that provides for capture of embolic material by the inner filter 52 while accommodating blood flow through the inner filter 52. The inner filter 52 can be made from any suitable material. For example, the inner filter 52 can be made from a porous polymer sheet. The inner filter 52 can have any suitable configuration. For example, in many embodiments, the inner filter 52 has an outer diameter in the fully deployed configuration equal to the inner diameter of the outer scaffold 44 in the fully deployed configuration. In many embodiments, the inner filter 52 has a longitudinal length and/or longitudinal flexibility that accommodates the change in length of the outer scaffold 44 between the insertion configuration and the fully deployed configuration. The inner filter 52 can be attached to the outer scaffold 44 using any suitable approach.

Figure 24:
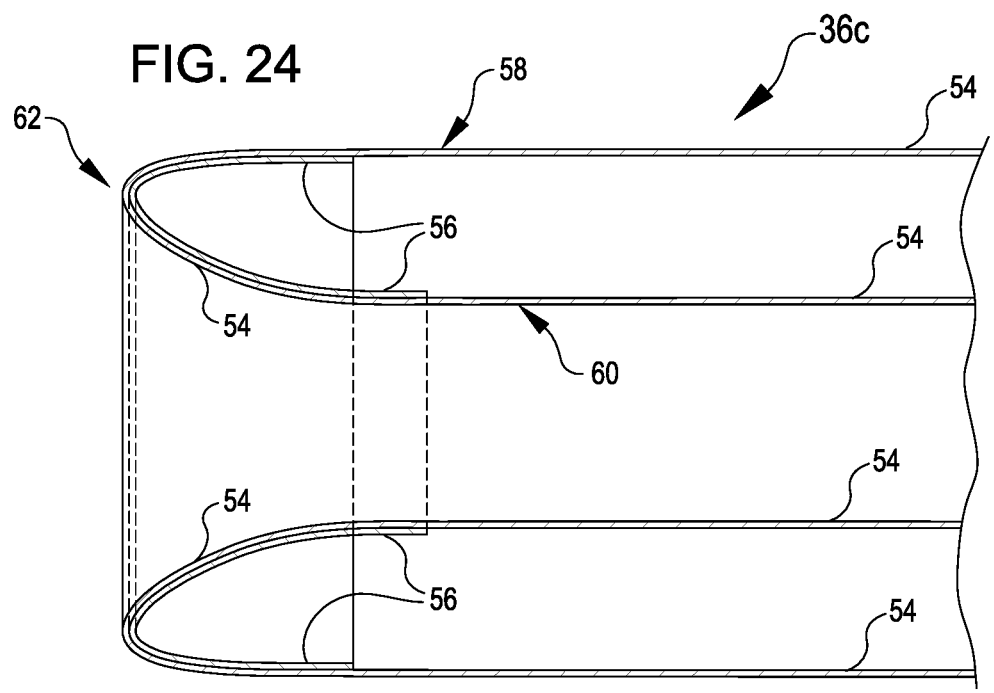
FIG. 24 shows a side cross-sectional view of a third configuration of the embolic material capture element of the embolic material capture catheter of FIG. 1.
Figure 25:
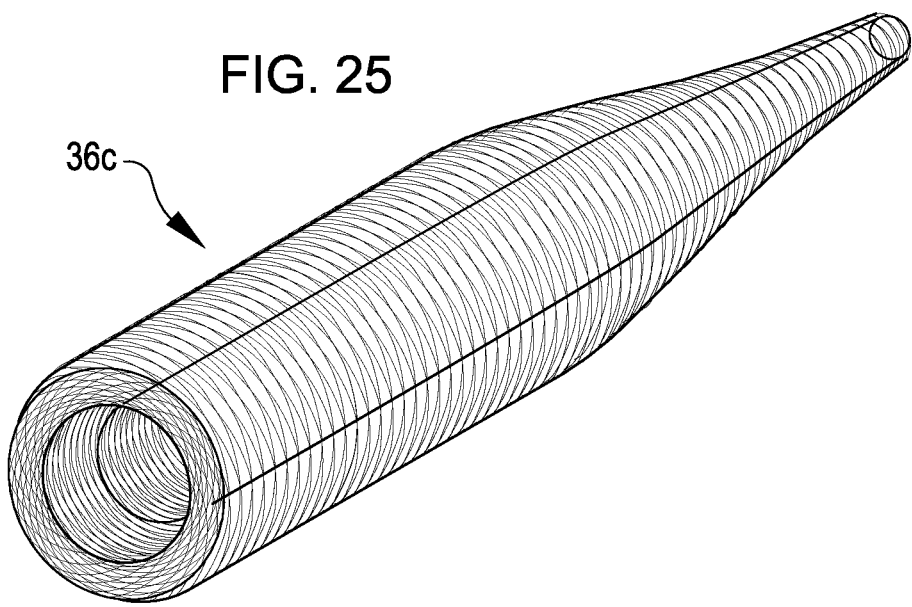
FIG. 25 shows an isometric view of the embolic material capture element of FIG. 24.

FIG. 24 shows a side cross-sectional view of a third configuration 36c of the embolic material capture element 36. The third configuration 36c of the embolic material capture element 36 includes a helically-braided shape memory alloy tube 54 and a distal end sheet 56. The braided shape memory alloy tube 54 is folded inside itself so as to have an outer tube portion 58, an inner tube portion 60, and a distal end portion 62 disposed between the outer tube portion 58 and the inner tube portion 60. The outer tube portion 58 can have any suitable diameter in the fully deployed configuration for use within a target blood vessel. For example, the outer tube portion 58 can have an outer diameter in the fully deployed configuration compatible with a target aorta anatomy. In many embodiments, the braided shape memory alloy tube 54 has a braided wire construction similar to the outer scaffold 44. In many embodiments, the porosity of the outer tube portion 58 in the fully deployed configuration is higher than the porosity of inner tube portion 60. In many embodiments, the diameter and/or the braid count of the inner tube portion 60 are selected to provide a suitable porosity for embolic material capture, for example, less than or equal to 150 microns. The distal end portion 62 can have a porosity that varies from the relatively higher porosity of the outer tube portion 58 to the porosity of the inner tube portion 60. The porosity of the outer tube portion 58 in the fully deployed configuration can be higher than the porosity of inner tube portion 60 due to the difference in diameters of the tube portions 58, 60. The maximum porosity of the braid can be calculated when the angle is at 90 degrees between the strands. The inner tube portion 60 can have a lower porosity for braid angles of the inner tube portion 60 that are greater than and less than 90 degrees, thereby producing diamond shape openings between the strands. The inner diameter of the inner tube portion 60 can be heat set to be large enough to accommodate the treatment catheter 100 and small enough so that the diamond shape of the crossing braid members has a porosity less than or equal to the target porosity. The distal end sheet 56 is attached to the distal end portion 62. The distal end sheet 56 can be nonporous or have a suitable porosity that provides for capture of embolic material by the distal end sheet 56 while accommodating blood flow through the distal end sheet 56. The distal end sheet 56 can be made from any suitable material. For example, the distal end sheet 56 can be formed from a solid polymer sheet or a porous laser cut polymer sheet. The distal end sheet 56 can be attached to the distal end portion 62 using any suitable approach. For example, the distal end sheet 56 can be laminated to the distal end portion 62 using any suitable approach. The distal end sheet 56 ensures that embolic material is prevented from passing through the distal end portion 62 and is funneled into the inner tube portion 54. FIG. 25 shows an isometric view of the third configuration 36c of the embolic material capture element 36.

Figure 26:
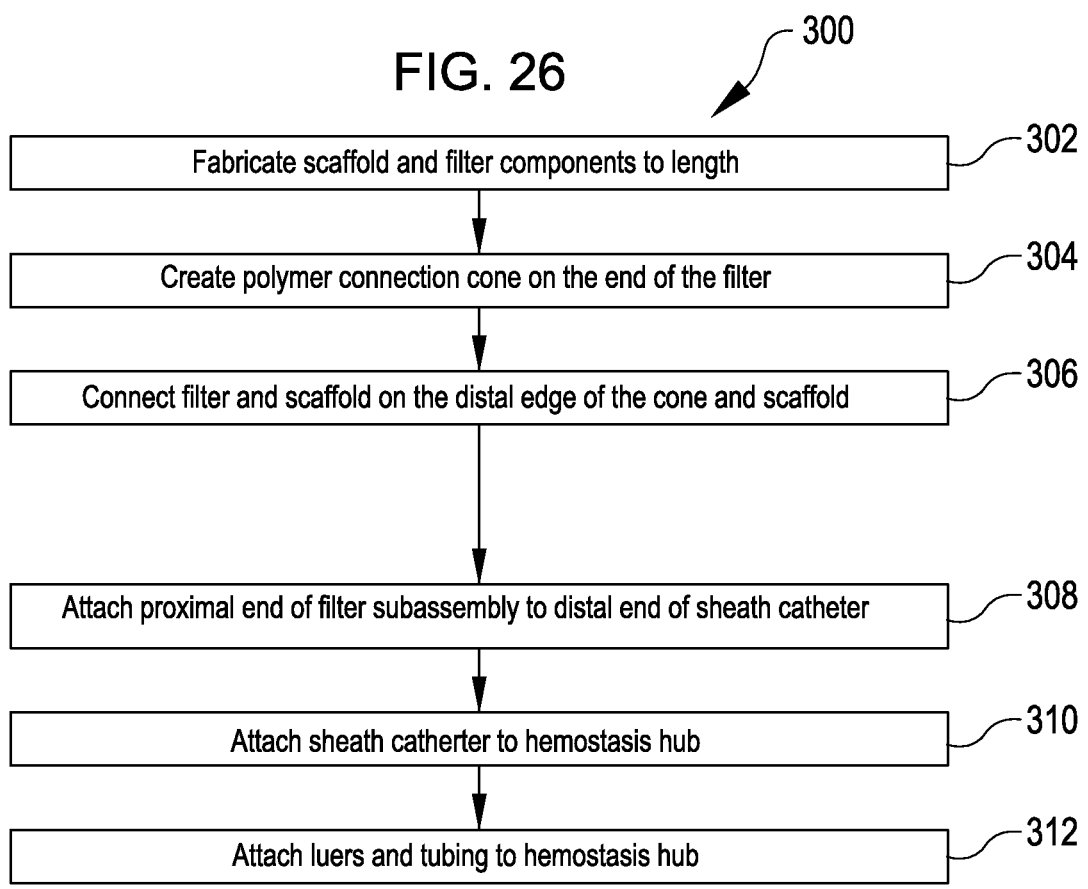
FIG. 26 is a simplified block diagram of acts of a method of fabricating the embolic material capture catheter of FIG. 1.

FIG. 26 shows a simplified schematic diagram of acts of a method 300 for fabricating embodiments the embolic material capture catheter 10. Acts 302, 304, and 306 are directed to fabricating the first configuration 36a of the embolic material capture element 36. Acts 308, 310, and 312 are directed to assembly of embodiments the embolic material capture catheter 10.

In act 302, the outer scaffold 44 and the inner filter 46 are fabricated to length using any suitable approach. For example, in many embodiments, the outer scaffold 44 is fabricated by helically winding and inter-braiding a suitable number of strands (e.g., 24-48 strands) of a suitable diameter (e.g., 0.006 to 0.010 inch) shape-memory wire (e.g., made from a suitable nickel-titanium shape memory alloy) at a suitable longitudinal pitch. In many embodiments, the strands of the wire 44w are helically-winded and inter-braided so that no ends of the strands are disposed at the distal end of the outer scaffold 44 to enhance the smoothness of the distal end of the outer scaffold 44. In many embodiments, the outer scaffold 44 is formed to have a fully-deployed configuration having a distal end external diameter a suitable amount larger than the diameter of the target blood vessel (e.g., aorta) so that, when deployed in the target blood vessel, the outer scaffold 44 will expand into engagement with the inner surface of the target blood vessel and exert a suitable radial force on the target blood vessel to maintain the position of the embolic material capture element 36 within the target blood vessel. In many embodiments, the inner filter 46 is fabricated by helically winding and inter-braiding a suitable number of strands (e.g., 288 strands) of a suitable diameter wire (e.g., 0.002 inch) of a suitable material (e.g., PET) at a suitable pitch. In many embodiments, the inner filter 46 is formed to have a fully-deployed configuration having a distal end external diameter a suitable amount smaller than the diameter of the target blood vessel (e.g., aorta) so that, when deployed in the target blood vessel, the inner filter 46 will be separated from the outer scaffold 44 by a suitably-sized annular space that accommodates flow of blood through the inner filter 46. In many embodiments, the outer scaffold 44 and the inner filter 46 are configured to longitudinally expand by substantially the same distance when reconfigured from the deployed configuration to the constrained insertion configuration, and to longitudinally contract by substantially the same distance when deployed from the constrained insertion configuration to the deployed configuration. The longitudinal expansion/contraction characteristics each of the outer scaffold 44 and the inner filter 46 can matched via suitable selection of parameters of the respective helical structures, such as longitudinal pitch and strand count, in view of the respective deployed diameters and the respective constrained insertion diameters. In act 304, the connection cone 48 is created on the end of the inner filter 46 using any suitable approach, such as the approach described herein with reference to FIG. 21. In act 306, the distal end of the connection cone 48 is connected to the distal end of the outer scaffold using any suitable approach, such as the approach described herein with reference to FIG. 21.

In act 308, the proximal end of the embolic material capture element 36 is attached to the distal end of the inner sheath 22 using any suitable approach. For example, the embolic material capture element 36 can be attached to the inner sheath 22 during fabrication of the inner sheath 22 or attached to the inner sheath 22 (e.g., to the inner diameter and/or to the outer diameter of the inner sheath 22) after the inner sheath 22 is fabricated. In some embodiments, the inner sheath 22 includes an inner liner (e.g., made from PTFE), a structural braid or coil (e.g., made from stainless steel, Nitinol, or monofilament), and an outer member polymer jacket (e.g., made from polyether block amide (PEBA), or nylon). The embolic material capture element 36 can be joined to the inner sheath 22 during fabrication of the inner sheath by disposing a proximal end portion of the embolic material capture element between the inner liner and the structural braid or coil of the inner sheath 22 or between the structural braid or coil and the outer member polymer jacket. The embolic material capture element 36 can be attached to the inner sheath 22 after fabrication of the inner sheath via a polymer sleeve (e.g., made from PEBA or nylon) to sandwich the proximal end portion of the inner filter 46 between the OD or ID of the distal end portion of the inner sheath 22 and the polymer sleeve. In act 310, the outer sheath 18 is attached to the outer sheath proximal end assembly 20 and the inner sheath 22 is attached to the inner sheath proximal end assembly 24. In act 312, Luers and tubing are attached to the proximal end assemblies 20, 24.

FIG. 27 shows a side view of an embodiment 36a-1 of the embolic material capture element 36a in the fully deployed configuration. FIG. 28 shows a side cross-sectional view of the embolic material capture element 36a-1 in the fully deployed configuration. In the fully deployed configuration, the embolic material capture element 36a-1 has a stepped outer diametrical profile configured to enhance deployment from the insertion configuration to the fully deployed configuration by substantially isolating contact between the outer scaffold 44 and the blood vessel to a distal end portion 64 of the embolic material capture element 36a-1. In the fully deployed configuration, a middle portion 66 of the embolic material capture element 36a-1 has a middle portion external diameter 68, and the distal end portion 64 has a distal end portion external diameter 70. In many embodiments, the distal end portion external diameter 70 is sized to provide a suitable amount of engagement with a target blood vessel. For example, the distal end portion external diameter 70 can be sized so that, in the fully deployed configuration, the distal end portion external diameter 70 would be a suitable increment larger than the inner diameter of the target blood vessel (e.g., aorta) so that the distal end portion 64 would exert a suitable interface pressure onto the target blood vessel when deployed in the target blood vessel. In many embodiments, the middle portion external diameter 68 is a suitably smaller than the inner diameter of the target blood vessel so that there is an annular clearance between the middle portion 66 and the inner wall of the target blood vessel to accommodate lengthwise contraction of the embolic material capture element 36a-1 during deployment from the insertion configuration to the fully deployed configuration by substantially isolating contact between the outer scaffold 44 and the blood vessel to the distal end portion 64. The annular clearance between the middle portion 66 and the inner wall of the target blood vessel serves to avoid interaction between the portion of the embolic material capture element 36a-1 proximal to the distal end portion 64 that might inhibit the contraction of the embolic material capture element 36a-1 during deployment from the insertion configuration to the fully deployed configuration. The middle portion external diameter 68, in the fully deployed configuration, can be any suitable amount smaller than the inner diameter of the target blood vessel or the distal end portion external diameter 70. For example, in the illustrated embodiment, the middle portion external diameter 68 is about 50 percent of the distal end portion external diameter 70.

The illustrated embodiment of the embolic material capture element 36a-1 includes a proximal connection cone 47 that connects the proximal end of the inner filter 46 to the distal end of the inner sheath 22. In many embodiments, the proximal connection cone 47 has a shape (e.g., conical) that provides for a smooth transition between the proximal end of the inner filter 46 and the distal end of the inner sheath 22. The proximal connection cone 47 can be made from any suitable material. For example, the proximal connection cone 47 can be formed from a suitable polymer sheet. The proximal connection cone 47 can be attached to the inner filter 46 and the inner sheath 22 using any suitable approach. For example, a distal end portion of the proximal connection cone 47 can be laminated to a corresponding proximal end portion of the inner filter 46; a proximal end portion of the proximal connection cone 47 can be attached to the distal end portion of the inner sheath 22. The proximal connection cone 47 can be nonporous or have a suitable porosity that provides for capture of embolic material by the proximal connection cone 47 while accommodating blood flow through the proximal connection cone 47. For example, a suitable porous proximal connection cone 47 can be formed from a laser cut polymer sheet.

In some embodiments of the embolic material capture element 36a-1, each of the connection cone 48 and/or the proximal connection cone 47 has a respective flexibility that accommodates differences between the amount of contraction of the outer scaffold 44 and the inner filter 46 during deployment from the insertion configuration to the fully deployed configuration. For example, each of the connection cone 48 and/or the proximal connection cone 47 can have a respective flexibility that accommodates changes in the longitudinal length of the connection cone 48 and/or the proximal connection cone 47 between the fully deployed configuration and the insertion configuration so as to accommodate differences between the amount of contraction of the outer scaffold 44 and the inner filter 46 during deployment from the insertion configuration to the fully deployed configuration.

FIG. 29 shows a side cross-sectional view of an embodiment 36c-1 of the embolic material capture element 36c in the fully deployed configuration. In the fully deployed configuration, the embolic material capture element 36c-1 has a stepped outer diametrical profile configured to enhance deployment from the insertion configuration to the fully deployed configuration by substantially isolating contact between the braided shape memory alloy tube 54 and the blood vessel to a distal end portion 72 of the embolic material capture element 36c-1. In the fully deployed configuration, a middle portion 74 of the embolic material capture element 36c-1 has a middle portion external diameter 76, and the distal end portion 72 has a distal end portion external diameter 78. In many embodiments, the distal end portion external diameter 78 is sized to provide a suitable amount of engagement with a target blood vessel. For example, the distal end portion external diameter 78 can be sized so that, in the fully deployed configuration, the distal end portion external diameter 78 would be a suitable increment larger than the inner diameter of a target blood vessel (e.g., aorta) so that the distal end portion 72 would exert a suitable interface pressure onto the target blood vessel when deployed in the target blood vessel. In many embodiments, the middle portion external diameter 76 is a suitably smaller than the inner diameter of the target blood vessel so that there is an annular clearance between the middle portion 74 and the inner wall of the target blood vessel to accommodate lengthwise contraction of the embolic material capture element 36c-1 during deployment from the insertion configuration to the fully deployed configuration by substantially isolating contact between the braided shape memory alloy tube 54 and the blood vessel to the distal end portion 72. The annular clearance between the middle portion 74 and the inner wall of the target blood vessel serves to avoid interaction between the portion of the embolic material capture element 36c-1 proximal to the distal end portion 72 that might inhibit the contraction of the embolic material capture element 36c-1 during deployment from the insertion configuration to the fully deployed configuration. The middle portion external diameter 76, in the fully deployed configuration, can be any suitable amount smaller than the inner diameter of the target blood vessel or the distal end portion external diameter 78. For example, in the illustrated embodiment, the middle portion external diameter 76 is about 50 percent of the distal end portion external diameter 78.

The devices and methods described herein are expected to produce substantial benefits in the way of substantially increased safety and efficacy of surgical treatments with a high likelihood of generation of embolic material, such as aortic valve replacement. As a result, such surgical treatments may be performed on a substantially increased number of patients with improve outcomes and reduce recovery times. Specifically, there will be less embolic material conveyed within the circulation system, thereby lowering the incidence of clinical stroke, subclinical stroke, silent cerebral embolization, renal embolization, mesenteric embolization, and peripheral embolization and each of the associated clinical syndromes.

The embolic material capture catheter 10 is suitable for use in procedures involving covered or uncovered stenting of arteries for capture and extraction of embolic material that may be liberated during their implantation for the treatment of aneurysms, dissections, stenosis or thrombus. The embolic material capture catheter 10 is suitable for prevention of injury resulting from embolic events occurring during balloon aortic valvuloplasty. The embolic material capture catheter 10 is suitable for prevention of tissue injury resulting from the performance of mitral balloon valvuloplasty or replacement. In the case of mitral procedures, the embolic protection provided by the embolic material capture catheter 10 may be separate from a delivery catheter. In this situation there may be a separate transvenous or transapical implantation system of sheaths and catheters for valve delivery and deployment and the embolic material capture catheter 10 can be deployed in the ascending aorta for capture and elimination of the material liberated from the mitral valve manipulation.

Other variations are within the spirit of the present invention. For example, the configurations 36a, 36b, 36c of the embolic material capture element 36 described herein can be deployed between an insertion configuration and a deployed configuration via relative movement of a restraining outer sheath without having the distal end of the embolic material capture element 36 separately constrained and subsequently released. For example, in some embodiments, an embolic material capture catheter for insertion into and advancement through a blood vessel of a patient includes the outer sheath assembly 12 and the inner sheath assembly 14, and does not include the dilator assembly 16. In such embodiments, the embolic material capture element 36 can be restrained in the insertion configuration via the outer sheath 18 during distal advancement through a blood vessel of a patient and then released for self-expansion from the insertion configuration to the deployed configuration via proximal retraction of the outer sheath assembly 12 relative to the inner sheath assembly 14. Such embodiments of an embolic material capture catheter (which do not include the dilator assembly 16) may be considerably shorter than embodiments that include the dilator assembly 26 and may be particularly suited for insertion via non-femoral access (e.g., trans-aortic access, trans-innominate access, or trans-subclavian access). Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

Examples of the embodiments of the present disclosure can be described in view of the following clauses:

Clause 1. An embolic material capture catheter comprising: an outer sheath defining an outer sheath lumen; an inner sheath slidably disposed in the outer sheath lumen and defining an inner sheath lumen; an embolic material capture element having a proximal end portion and a distal end portion, the proximal end portion being attached to a distal end portion of the inner sheath, the embolic material capture element having an insertion configuration, an intermediate deployment configuration, and a fully deployed configuration; the embolic material capture element being adapted to, in the fully deployed configuration, interface with an inner surface of a blood vessel; the embolic material capture element being adapted to block flow of embolic material through the blood vessel past the embolic material capture element; and a dilator assembly including a dilator sheath and a deployment cap assembly, the dilator sheath being slidably disposed in the inner sheath lumen and defining a dilator sheath lumen, the deployment cap assembly being slidably disposed in the dilator sheath lumen, wherein: a distal end portion of the embolic material capture element is restrained in the insertion configuration and the intermediate deployment configuration by the dilator assembly, a middle portion of the embolic material capture element expands radially from the insertion configuration to the intermediate deployment configuration via distal advancement of the inner sheath towards the distal end portion of the embolic material capture element restrained by the dilator assembly, the distal end portion of the embolic material capture element expands radially from the intermediate deployment configuration to the fully deployed configuration in response to release of the distal end portion of the embolic material capture element by the dilator assembly via distal advancement of the deployment cap assembly relative to the dilator sheath, and the dilator assembly is removable from the inner sheath lumen while the embolic material capture element is in the fully deployed configuration via proximal retraction of the dilator assembly relative to the inner sheath.

Clause 2. The embolic material capture catheter of clause 1, wherein the embolic material capture element is reconfigurable from the fully deployed configuration to a captured configuration in which the embolic material capture element is disposed in the outer sheath lumen via proximal retraction of the inner sheath relative to the outer sheath.

Clause 3. The embolic material capture catheter of any preceding clause, wherein the embolic material capture element conforms to an outer surface of the dilator sheath from the proximal end portion of the embolic material capture element to the distal end portion of the embolic material capture element when the embolic material capture element is in the insertion configuration.

Clause 4. The embolic material capture catheter of any preceding clause, wherein: the embolic material capture element has an outer surface that extends between the proximal end portion of the embolic material capture element and the distal end portion of the embolic material capture element; and the outer surface of the embolic material capture element is disposable distal to the outer sheath with the embolic material capture element in the insertion configuration.

Clause 5. The embolic material capture catheter of any preceding clause, wherein the embolic material capture element comprises a shape-memory material.

Clause 6. The embolic material capture catheter of clause 5, wherein the embolic material capture element is retained in the insertion configuration at least partially via axial tension imparted into the embolic material capture element via the dilator assembly.

Clause 7. The embolic material capture catheter of any preceding clause, wherein: the inner sheath accommodates insertion of a treatment catheter into the inner sheath lumen and advancement of a distal portion of the treatment catheter to a position distal to the distal end portion of the embolic material capture element in the fully deployed configuration; and the distal end portion of the treatment catheter is adapted to accomplish a surgical task.

Clause 8. The embolic material capture catheter of clause 7, wherein: the embolic material capture element is adapted to, in the fully deployed configuration, interface with a patient's aorta and substantially block flow of embolic material through the patient's aorta past the embolic material capture element; and the treatment catheter is adapted to deploy a prosthetic aortic valve.

Clause 9. The embolic material capture catheter of any preceding clause, wherein the embolic material capture element comprises a filtering membrane adapted to filter embolic material from blood flowing through the filtering membrane.

Clause 10. The embolic material capture catheter of any preceding clause, adapted to be coupled with an embolic material extraction device operable to draw embolic material through the inner sheath lumen while the embolic material capture element is in the fully deployed configuration.

Clause 11. The embolic material capture catheter of any preceding clause, wherein the embolic material capture element comprises an outer support element and an inner filter element attached to the outer support element, the outer support element including one or more members that radially expand into contact with the wall of a vessel along which embolic material is blocked from traversing, the inner filter element being configured to prevent emboli of greater than a particular size from passing through the inner filter element.

Clause 12. The embolic material capture catheter of any preceding clause, wherein the embolic material capture element comprises an outer scaffold portion, an inner filter portion, and an intermediate portion; the outer scaffold portion having an outer scaffold proximal end portion and an outer scaffold distal end portion; the outer scaffold proximal end portion being attached to the filter sheath distal end portion; the outer scaffold portion being configured to self-expand during reconfiguration of the embolic material capture catheter from the restrained insertion configuration to the deployed configuration for engagement with a blood vessel inner surface; the inner filter portion having an inner filter proximal end portion and an inner filter distal end portion; the inner filter proximal end portion being attached to the filter sheath distal end portion; the inner filter portion being configured to capture embolic material from blood that flows through the inner filter portion; the inner filter distal end portion being coupled with the outer scaffold distal end portion via the intermediate portion.

Clause 13. The embolic material capture catheter of clause 12, wherein the inner filter portion is separated from the outer scaffold portion by an intervening annular space in the deployed configuration.

Clause 14. The embolic material capture catheter of clause 13, wherein the intermediate portion is configured to capture embolic material from blood flowing through the intermediate portion.

Clause 15. The embolic material capture catheter of clause 13, wherein the intermediate portion is nonporous.

Clause 16. The embolic material capture catheter of any one of clause 13 through clause 15, wherein the intermediate portion has a conical shape configured to direct blood flow into the inner filter portion.

Clause 17. The embolic material capture catheter of any one of clause 13 through clause 16, wherein the outer scaffold portion, the intermediate portion, and the inner filter portion are portions of an integrally formed braided wire member.

Clause 18. The embolic material capture catheter of clause 17, further comprising a distal end sheet attached to the intermediate portion, the distal end sheet being configured to block flow of embolic material through the intermediate portion.

Clause 19. The embolic material capture catheter of clause 18, wherein the distal end sheet is nonporous.

Clause 20. The embolic material capture catheter of clause 18, wherein the distal end sheet has a porosity adapted to filter embolic material out of blood flowing through the distal end sheet.

Clause 21. The embolic material capture catheter of any one of clause 13 through clause 20, wherein the outer scaffold portion comprises distally extending loops of wires configured for atraumatic engagement of the blood vessel inner surface.

Clause 22. A method of deploying an embolic material capture element in a blood vessel, the method comprising: constraining a proximal end portion of an embolic material capture element via attachment to a distal end portion of an inner sheath having an inner sheath lumen; constraining a distal end portion of the embolic material capture element in an insertion configuration of the embolic material capture element and an intermediate deployment configuration of the embolic material capture element via engagement of the distal end portion of the embolic material capture element with a dilator assembly that extends through the inner sheath lumen; advancing the embolic material capture element in the insertion configuration through the blood vessel; reconfiguring the embolic material capture element from the insertion configuration to the intermediate deployment configuration by expanding a middle portion of the embolic material capture element disposed between the proximal end portion of the embolic material capture element and the distal end portion of the embolic material capture element via distal advancement of the inner sheath toward the distal end portion of the embolic material capture element constrained by the dilator assembly; and reconfiguring the embolic material capture element from the intermediate deployment configuration to the fully deployed configuration via reconfiguration of the dilator assembly to release the distal end portion of the embolic material capture element from engagement with the dilator assembly and self-expansion of the distal end portion of the embolic material capture element.

Clause 23. The method of clause 22, further comprising reconfiguring the embolic material capture element from the fully deployed configuration to a captured configuration via proximal retraction of the inner sheath relative to an outer sheath to retract the embolic material capture element within an outer sheath lumen of the outer sheath.

Clause 24. The method of any one of clause 22 and clause 23, wherein the embolic material capture element conforms to an outer surface of the dilator assembly from the proximal end portion of the embolic material capture element to the distal end portion of the embolic material capture element when the embolic material capture element is in the insertion configuration.

Clause 25. The method of any one of clause 22 through clause 24, wherein: the embolic material capture element has an outer surface that extends between the proximal end portion of the embolic material capture element and the distal end portion of the embolic material capture element; and the outer surface of the embolic material capture element is disposable distal to the outer sheath when the embolic material capture element is advanced through the blood vessel in the insertion configuration.

Clause 26. The method of any one of clause 22 through clause 25, wherein the embolic material capture element comprises a shape-memory material.

Clause 27. The method of any one of clause 22 through clause 26, comprising retaining the embolic material capture element in the insertion configuration at least partially via axial tension imparted into the embolic material capture element via the dilator assembly.

Clause 28. The method of any one of clause 22 through clause 27, further comprising: advancing a distal portion of a treatment catheter through the inner sheath lumen to a position distal to the distal end portion of the embolic material capture element in the fully deployed configuration; and accomplishing a surgical task distal to the distal end of the embolic material capture element in the fully deployed configuration via the treatment catheter.

Clause 29. The method of clause 28, comprising: interfacing the embolic material capture element in the fully deployed configuration with a patient's aorta; blocking flow of embolic material through the patient's aorta past the embolic material capture element; and deploying a prosthetic aortic valve from the distal end portion of the treatment catheter.

Clause 30. The method of any one of clause 22 through clause 29, wherein: the embolic material capture element comprises a filtering membrane; and the method comprises filtering embolic material from blood flowing through the blood vessel via the filtering membrane.

Clause 31. The method of any one of clause 22 through clause 30, comprising extracting embolic material through the inner sheath lumen while the embolic material capture element is in the fully deployed configuration.

Clause 32. An embolic material capture catheter having a restrained insertion configuration and a deployed configuration, the embolic material capture catheter comprising: a filter sheath having an inner lumen and a filter sheath distal end portion; and a filter assembly attached to the filter sheath distal end portion; the filter assembly comprising an outer scaffold portion, an inner filter portion, and an intermediate portion; the outer scaffold portion having an outer scaffold proximal end portion and an outer scaffold distal end portion; the outer scaffold proximal end portion being attached to the filter sheath distal end portion; the outer scaffold portion being configured to self-expand during reconfiguration of the embolic material capture catheter from the restrained insertion configuration to the deployed configuration for engagement with a blood vessel inner surface; the inner filter portion having an inner filter proximal end portion and an inner filter distal end portion; the inner filter proximal end portion being attached to the filter sheath distal end portion; the inner filter portion being configured to capture embolic material from blood that flows through the inner filter portion; the inner filter distal end portion being coupled with the outer scaffold distal end portion via the intermediate portion.

Clause 33. The embolic material capture catheter of clause 32, wherein the inner filter portion is separated from the outer scaffold portion by an intervening annular space in the deployed configuration.

Clause 34. The embolic material capture catheter of clause 33, wherein the intermediate portion is configured to capture embolic material from blood flowing through the intermediate portion.

Clause 35. The embolic material capture catheter of clause 33, wherein the intermediate portion is nonporous.

Clause 36. The embolic material capture catheter of any one of clause 33 through clause 35, wherein the intermediate portion has a conical shape configured to direct blood flow into the inner filter portion.

Clause 37. The embolic material capture catheter of any one of clause 33 through clause 36, wherein the outer scaffold portion, the intermediate portion, and the inner filter portion are portions of an integrally formed braided wire member.

Clause 38. The embolic material capture catheter of clause 37, further comprising a distal end sheet attached to the intermediate portion, the distal end sheet being configured to block flow of embolic material through the intermediate portion.

Clause 39. The embolic material capture catheter of clause 38, wherein the distal end sheet is nonporous.

Clause 40. The embolic material capture catheter of clause 38, wherein the distal end sheet has a porosity adapted to filter embolic material out of blood flowing through the distal end sheet.

Clause 41. The embolic material capture catheter of any one of clause 33 through clause 40, wherein the outer scaffold portion comprises distally extending loops of wires configured for atraumatic engagement of the blood vessel inner surface.

Clause 42. An embolic material capture catheter having a restrained insertion configuration and a deployed configuration, the embolic material capture catheter comprising: a filter sheath having an inner lumen and a filter sheath distal end portion; and a filter assembly attached to the filter sheath distal end portion, the filter assembly comprising an outer scaffold portion and an inner filter portion, the outer scaffold portion having an outer scaffold proximal end portion and an outer scaffold distal end portion, the outer scaffold proximal end portion being attached to the filter sheath distal end portion, the outer scaffold portion being configured to self-expand during reconfiguration of the embolic material capture catheter from the restrained insertion configuration to the deployed configuration for engagement with a blood vessel inner surface, the inner filter portion having an inner filter proximal end portion; the inner filter portion being attached to outer scaffold portion, the inner filter portion being configured to capture embolic material from blood that flows through the inner filter portion.

Clause 43. The embolic material capture catheter of clause 42, wherein the inner filter portion is attached to the outer scaffold portion along an entire length of the outer scaffold portion.

What is claimed is:

1. A method of deploying an embolic material capture element in a blood vessel, the method comprising:
constraining a proximal end portion of an embolic material capture element via attachment to a distal end portion of an inner sheath having an inner sheath lumen, wherein the embolic material capture element comprises a filtering membrane;
constraining a distal end portion of the embolic material capture element in an insertion configuration of the embolic material capture element via engagement of the distal end portion of the embolic material capture element with a dilator assembly that extends through the inner sheath lumen, wherein the dilator assembly comprises a dilator sheath and a deployment cap assembly, wherein the dilator sheath defines a dilator sheath lumen, and wherein the deployment cap assembly is slidably disposed in the dilator sheath lumen;
advancing the embolic material capture element in the insertion configuration through the blood vessel;
distally advancing the deployment cap assembly relative to the dilator sheath to release the distal end portion of the embolic material capture element from engagement with the dilator assembly to reconfigure the embolic material capture element from the insertion configuration to a fully deployed configuration via self-expansion of the embolic material capture element; and
filtering embolic material from blood flowing through the blood vessel via the filtering membrane.

2. The method of claim 1, further comprising reconfiguring the embolic material capture element from the fully deployed configuration to a captured configuration via proximal retraction of the inner sheath relative to an outer sheath to retract the embolic material capture element within an outer sheath lumen of the outer sheath.

3. The method of claim 2, wherein:
the embolic material capture element has an outer surface that extends between the proximal end portion of the embolic material capture element and the distal end portion of the embolic material capture element; and
the outer surface of the embolic material capture element is disposable distal to the outer sheath when the embolic material capture element is advanced through the blood vessel in the insertion configuration.

4. The method of claim 1, wherein the embolic material capture element conforms to an outer surface of the dilator assembly from the proximal end portion of the embolic material capture element to the distal end portion of the embolic material capture element when the embolic material capture element is in the insertion configuration.

5. The method of claim 1, wherein the embolic material capture element comprises a shape-memory material.

6. The method of claim 5, comprising retaining the embolic material capture element in the insertion configuration at least partially via axial tension imparted into the embolic material capture element via the dilator assembly.

7. The method of claim 1, further comprising:
advancing a distal portion of a treatment catheter through the inner sheath lumen to a position distal to the proximal end portion of the embolic material capture element in the fully deployed configuration; and
accomplishing a surgical task distal to the proximal end portion of the embolic material capture element in the fully deployed configuration via the treatment catheter.

8. The method of claim 7, comprising:
interfacing the embolic material capture element in the fully deployed configuration with a patient's aorta;
blocking flow of embolic material through the patient's aorta past the embolic material capture element; and
deploying a prosthetic aortic valve from the distal end portion of the treatment catheter.

9. The method of claim 1, comprising reconfiguring the embolic material capture element from the insertion configuration to an intermediate deployment configuration by expanding a middle portion of the embolic material capture element disposed between the proximal end portion of the embolic material capture element and the distal end portion of the embolic material capture element via distal advancement of the inner sheath toward the distal end portion of the embolic material capture element constrained by the dilator assembly.

10. The method of claim 1, comprising drawing embolic material through the inner sheath lumen while the embolic material capture element is in the fully deployed configuration.

11. The method of claim 1, wherein the embolic material capture element comprises an outer support element and an inner filter element attached to the outer support element, the outer support element including one or more members that radially expand into contact with a wall of a vessel along which embolic material is blocked from traversing, the inner filter element being configured to prevent emboli of greater than a particular size from passing through the inner filter element.

12. The method of claim 1, wherein:
the embolic material capture element comprises an outer scaffold portion, an inner filter portion, and an intermediate portion;
the outer scaffold portion has an outer scaffold proximal end portion and an outer scaffold distal end portion;
the outer scaffold proximal end portion is attached to the distal end portion of the inner sheath;
the outer scaffold portion is configured to self-expand during reconfiguration of the embolic material capture element from the insertion configuration to the fully deployed configuration for engagement with a blood vessel inner surface;
the inner filter portion has an inner filter proximal end portion and an inner filter distal end portion;
the inner filter proximal end portion is attached to the distal end portion of the inner sheath;
the inner filter portion is configured to capture embolic material from blood that flows through the inner filter portion; and
the inner filter distal end portion is coupled with the outer scaffold distal end portion via the intermediate portion.

13. The method of claim 12, wherein the inner filter portion is separated from the outer scaffold portion by an intervening annular space in the fully deployed configuration.

14. The method of claim 13, wherein the intermediate portion is configured to capture embolic material from blood flowing through the intermediate portion.

15. The method of claim 13, wherein the intermediate portion is nonporous.

16. The method of claim 13, wherein the intermediate portion has a conical shape configured to direct blood flow into the inner filter portion.

17. The method of claim 13, wherein the outer scaffold portion, the intermediate portion, and the inner filter portion are portions of an integrally formed braided wire member.

18. The method of claim 17, wherein the embolic material capture element comprises a distal end sheet attached to the intermediate portion, the distal end sheet being configured to block flow of embolic material through the intermediate portion.

19. The method of claim 13, wherein the outer scaffold portion comprises distally extending loops of wires configured for atraumatic engagement of the blood vessel inner surface.

20. The method of claim 1, wherein:
a middle portion of the embolic material capture element has a middle portion external diameter in the fully deployed configuration;
the distal end portion of the embolic material capture element has a distal end portion external diameter in the fully deployed configuration; and
the middle portion external diameter is less than the distal end portion external diameter.

21. The method of claim 1, wherein:
the embolic material capture element comprises an outer scaffold portion and an inner filter portion; and
the inner filter portion is separated from the outer scaffold portion by an intervening annular space in the fully deployed configuration along a length of the inner filter portion.

* * * * *